United States Patent [19]

Cage et al.

[11] Patent Number: 5,473,949
[45] Date of Patent: Dec. 12, 1995

[54] CORIOLIS MASS FLOW RATE METER HAVING ADJUSTABLE PRESSURE AND DENSITY SENSITIVITY

[75] Inventors: Donald R. Cage, Longmont; Michael N. Schott, Loveland, both of Colo.

[73] Assignee: Direct Measurement Corporation, Longmont, Colo.

[21] Appl. No.: 402,189

[22] Filed: Mar. 10, 1995

Related U.S. Application Data

[60] Division of Ser. No. 233,687, Apr. 26, 1994, which is a continuation-in-part of Ser. No. 83,975, Jun. 28, 1993, abandoned, and a continuation-in-part of Ser. No. 843,519, May 8, 1992, abandoned, and a continuation-in-part of Ser. No. 651,301, Feb. 5, 1991, abandoned.

[51] Int. Cl.⁶ .................................................. G01F 1/84
[52] U.S. Cl. .................... 73/861.38; 73/861.37; 73/32 A
[58] Field of Search .................... 73/861.01, 861.02, 73/861.37, 861.38, 32 R, 32 A

[56] References Cited

U.S. PATENT DOCUMENTS

| | | | |
|---|---|---|---|
| Re. 31,450 | 11/1983 | Smith | 73/861.38 |
| 3,444,723 | 5/1969 | Wakefield | 73/32 |
| 3,485,098 | 12/1969 | Sipin | 73/194 |
| 3,927,565 | 12/1975 | Pavlin et al. | 73/194 |
| 4,009,616 | 3/1977 | Wonn | 73/398 R |
| 4,109,524 | 8/1978 | Smith | 73/194 |
| 4,420,983 | 12/1983 | Langdon | 73/861.18 |
| 4,422,338 | 12/1983 | Smith | 73/861.38 |
| 4,491,025 | 1/1985 | Smith et al. | 73/861.38 |
| 4,574,639 | 3/1986 | Ward | 73/702 |
| 4,622,858 | 11/1986 | Mizerak | 73/861.38 |
| 4,628,744 | 12/1986 | Lew | 73/861.38 |
| 4,653,332 | 3/1987 | Simonsen | 73/861.38 |
| 4,680,974 | 7/1987 | Simonsen et al. | 73/861.38 |
| 4,691,578 | 9/1987 | Herzl | 73/861.38 |
| 4,711,132 | 12/1987 | Dahlin | 73/861.38 |

(List continued on next page.)

FOREIGN PATENT DOCUMENTS

| | | |
|---|---|---|
| 40119638 | 9/1984 | European Pat. Off. |
| WO85/05677 | 12/1985 | European Pat. Off. |
| 57-137818 | 8/1982 | Japan . |
| 1008617A | 2/1980 | Sudan . |
| 2171200 | 8/1986 | United Kingdom . |

OTHER PUBLICATIONS

Publication entitled "Direkte Massedurchflussmessung, Insbesonderemit Coriolisverfahren" by Von W. Steffen und Dr. W. Stumm; Part II; pp. 301–305; Published in "Messen Prüfen Automatisieren" vol. 23 (1987) May, No. 5, pp. 301–305; Bad Wörishofen, W. Germany.

*Primary Examiner*—Thomas P. Noland
*Assistant Examiner*—Harshad Patel
*Attorney, Agent, or Firm*—Hitt Chwang & Gaines

[57] ABSTRACT

Several Radial Mode Coriolis mass flow rate meter geometries and electronic circuits are described that may be made to be sensitive to pressure or density changes. In one embodiment, the meter comprises: (1) a flow conduit for containing a fluid having a physical characteristic, the fluid adapted to flow in the conduit at an unknown rate, (2) a drive circuit for creating a vibration in the flow conduit, the fluid altering the vibration as a function of the physical characteristic and the flow rate, (3) a detector circuit for measuring the altered vibration at a working point and producing a signal representing an uncompensated mass flow rate of the fluid and (4) a computation circuit for calculating a compensated mass flow rate of the fluid proportional to the uncompensated rate by $1/\Omega 1^n$, where $\Omega 1$ is a driven natural frequency of the flow conduit and n is a number chosen as a function of the working point, the compensated rate thereby reduced of effects of the physical characteristic. A unique mathematical algorithm is also described that allows for a much wider variety of design geometry while maintaining insensitivity to pressure or density without having to measure or compensate for either. In addition, a method is described that allows for the accurate measurement and compensation of both pressure and density.

3 Claims, 12 Drawing Sheets

U.S. PATENT DOCUMENTS

| | | | |
|---|---|---|---|
| 4,716,771 | 1/1988 | Kane | 73/861.38 |
| 4,729,243 | 3/1988 | Friedland et al. | 73/861.38 |
| 4,733,569 | 3/1988 | Kelsey et al. | 73/861.38 |
| 4,756,197 | 7/1988 | Herzl | 73/861.38 |
| 4,768,384 | 9/1988 | Flecken et al. | 73/861.02 |
| 4,776,220 | 10/1988 | Lew | 73/861.38 |
| 4,793,191 | 12/1988 | Flecken et al. | 73/861.38 |
| 4,798,091 | 1/1989 | Lew | 73/861.38 |
| 4,803,867 | 2/1989 | Dahlin | 73/32 |
| 4,811,606 | 3/1989 | Hasegawa et al. | 73/861.38 |
| 4,813,289 | 3/1989 | Lew | 73/861.38 |
| 4,823,613 | 4/1989 | Cage et al. | 73/861.38 |
| 4,823,614 | 4/1989 | Lew | 73/861.38 |
| 4,829,832 | 5/1989 | Lew | 73/861.38 |
| 4,831,885 | 5/1989 | Dahlin | 73/861.38 |
| 4,852,410 | 8/1989 | Corwon et al. | 73/861.38 |
| 4,856,346 | 8/1989 | Kane | 73/861.38 |
| 4,869,097 | 9/1989 | Tittmann et al. | 73/52 |
| 4,879,910 | 11/1989 | Lew | 73/861.37 |
| 4,882,935 | 11/1989 | Lew | 73/861.38 |
| 4,891,991 | 1/1990 | Mattar et al. | 73/861.38 |
| 4,934,195 | 6/1990 | Hussain | 73/861.38 |
| 4,949,583 | 8/1990 | Lang et al. | 73/861.37 |
| 5,024,104 | 6/1991 | Dames | 73/861.37 |
| 5,040,415 | 8/1991 | Barkhoudarian | 73/198 |
| 5,044,207 | 9/1991 | Atkinson et al. | 73/861.37 |
| 5,069,075 | 12/1991 | Hansen et al. | 73/861.38 |
| 5,226,330 | 7/1993 | Lew | 73/861.37 |
| 5,230,254 | 7/1993 | Craft | 73/861.38 |
| 5,259,250 | 11/1993 | Kotpak | 73/861.38 |
| 5,373,745 | 12/1994 | Cage | 73/861.37 |

CORIOLIS MASS FLOW RATE METER HAVING ADJUSTABLE PRESSURE AND DENSITY SENSITIVITY

CROSS-REFERENCE TO RELATED APPLICATIONS

This application is a division of Ser. No. 08/233,687 filed on Apr. 26, 1994, which is a continuation-in-part of Ser. No. 08/083,975 filed on Jun. 28, 1993, now abandoned, a continuation-in-part of Ser. No. 07/843,519, filed on May 8, 1992, now abandoned, a continuation-in-part of Ser. No. 07/651,301, filed on Feb. 5, 1991, now abandoned, all of which are commonly assigned with the present invention and are incorporated herein by reference.

TECHNICAL FIELD OF THE INVENTION

The present invention is directed, in general, to mass flow rate meters incorporating measurement of Coriolis forces and, more specifically, to such meters that, by virtue of their geometry, associated compensation circuitry or both, are rendered substantially insensitive to fluid pressure and density.

BACKGROUND OF THE INVENTION

During the last 15 years a new flow meter technology has evolved using vibrating conduits and Coriolis forces developed in fluids flowing therein to measure the mass flow rate of a fluid. A typical sensor employs two parallel conduits usually bent into some unique shape such as a "U" or an "S" or a bowtie shape. These conduits are normally welded to a rigid casting at their inlets and outlets and the conduits are forced to vibrate with one conduit vibrating in opposition to the other for balance purposes. Fluid flowing through the vibrating conduits therefore experiences this vibrating motion and, in particular, the angular rotation of the conduits, causing Coriolis forces to impinge on the walls of these conduits. The net effect is a slight deformation and deflection of the conduit proportional to the mass flow rate of the fluid, the angular velocity of the conduits and some conduit geometry constants. This deformation exemplifies itself and is normally measured as a small phase or time delay between the deflection at the inlet ends of the conduits compared to the deflection at the outlet ends.

Since its inception and reduction to practice in industry, many innovative methods and inventions have been employed to maximize these tiny deflections and their time delays to improve the sensitivity of these devices. Many of these efforts have focused on improving the shape of the bent conduits to maximize angular rotational velocity while minimizing the stiffness that opposes the Coriolis deflections. This line of reasoning has led to many innovative shapes that lengthen these phase delays, however the design tradeoffs are generally, (a) a complex conduit shape to bend, (b) thinner walled flow conduits, (c) a lower frequency of operation, creating susceptibility to ambient vibrations and (d) a higher pressure drop through the device due to introduction of flow splitters and complex conduit geometry. Some examples of these flow conduit geometries are the dual S-conduits of U.S. Pat. Nos. 4,798,091 and 4,776,220 to Lew, the Ω-shaped conduits of U.S. Pat. No. 4,852,410 to Corwon, et al., the B-shapes conduits of U.S. Pat. No. 4,891,991 to Mattar, et al., the helically-wound flow conduits of U.S. Pat. No. 4,756,198 to Levien, figure-8 shaped flow conduits of U.S. Pat. No. 4,716,771 to Kane and the dual straight conduits of U.S. Pat. No. 4,680,974 to Simonsen, et al.. These complex conduit shapes also contribute to the overall size of the device and usually preclude the ability to place the device within a reasonably-sized pressure-containing case for safety reasons. In addition to the problems associated with the general shape of the conduits, the magnitude and placement of masses on the conduits (such as magnets), for the purposes of driving and sensing the requisite vibratory motions, can adversely affect the response of the device to flow rate under the conditions of changing pressure, density or both.

Currently, several new types of Coriolis flow meters are being developed using radial vibratory motion of the wall of a single straight conduit, with flow going either within or around the conduit, thereby eliminating the flow splitters and the second counterbalancing flow conduit. Such meters are referred to as "radial mode meters."

A Coriolis mass flow meter sensor is a device that accommodates the flow of fluid within or around one or more flow conduits and subjects that flowing fluid to an angular rotation by virtue of a vibration or oscillatory motion of the flow conduit(s). The flow conduit(s) are normally designed to be highly resonant devices that can be easily excited to vibrate in one or more natural modes of vibration for this purpose. This angular rotation imparted into the flowing fluid by this conduit motion thus causes resultant Coriolis forces to develop and bear against the sidewalls of the flow conduit in a direction that is 90° from both the angular rotation vector and the fluid velocity vector. These resulting forces are cyclic in nature (normally sinusoidal) at the frequency of the excitation motion.

Since these devices are normally designed to be highly resonant and compliant structures, the resulting sinusoidal Coriolis force distribution results in a sinusoidal (as a function of time) deflection of the structure that is proportional to the mass flow rate of the fluid and the frequency response of the structure for that given excitation. As stated previously, the frequency response of the device can change as a function of fluid pressure, density, temperature and conduit stress, it is essential that it be accurately known and compensated for, or held to be constant to achieve accurate mass flow rate measurements from the device. Therefore, one aspect of the present invention is the ability to control the response of a flow conduit geometry to achieve insensitivity to these changing parameters by virtue of the flow conduit's geometry in combination with a motion measurement method. This arrangement implemented on a radial mode meter has many advantages over the bending mode meter types previously described and virtually solves the design tradeoffs (a) through (d) previously mentioned. While both radial mode and bending mode meters can exhibit pressure sensitivity, the problem is generally more severe on radial mode Coriolis meters because internal fluid pressure tends to stiffen the walls of the conduit with regard to radial vibrations more than with regard to bending mode vibrations. In addition, radial mode meters generally have vibration frequencies that are orders of magnitude higher and have flow-related phase or time delays that are many times smaller than traditional bending mode Coriolis flow meters. For example, a typical 1" bending mode Coriolis flow meter operates at approximately 100 Hz while a typical 1" radial mode meter operates above 3000 Hz. Consequently, the Coriolis signal-processing method of choice traditionally has been a phase or time delay measurement. Unfortunately, measuring phase or time delay results in very poor sensitivity and resolution for radial mode meters. For example, a typical time delay measured at a nominal flow rate on a traditional bending mode flow meter is in the tens of microseconds and easily measured with today's electronics. By contrast, the same flow rate in a comparable radial mode Coriolis meter might cause only tens of nanoseconds of time delay, a period of time that is much more difficult and expensive to measure accurately. To date, the only radial mode Coriolis flow meter patent has been that of Lang (U.S. Pat. No. 4,949,583) who describes a radial mode vibrating sensor. However, Lang exclusively uses a relative phase displacement measuring technique requiring signal processing circuitry designed to discern minuscule time delays. Such circuitry is relatively expensive and inaccurate, damaging the efficacy of the meter as a whole. Consequently, to date no practical device has yet been disclosed or marketed for commercial applications.

Therefore, the current invention addresses the more general task of providing a Coriolis flow meter that is insensitive to both density and pressure at the same time.

SUMMARY OF THE INVENTION

The present invention was therefore discovered, developed and applied to solve the pressure, density and small signal problems with regard to prior art radial mode Coriolis flow meters and was subsequently found to be relevant to traditional bending mode meters as well.

Using the present invention therefore, a Coriolis mass flow meter is provided that solves the previously-mentioned design tradeoffs and is insensitive to changing fluid parameters of pressure, density, temperature, or any combination thereof by using either of three embodiments to achieve this end.

The first embodiment involves construction of a unique flow meter geometry according to the present invention that has the property of being inherently insensitive to changing fluid properties. In this first embodiment, the meter comprises: (1) a flow conduit for containing a fluid having a pressure and density, the fluid adapted to flow in the conduit at an unknown rate, the flow conduit composed of a desired material and having a desired length, radius and wall thickness, (2) a drive circuit for creating a vibration in the flow conduit, the fluid altering the vibration as a function of the flow rate, the desired material, length, radius and wall thickness yielding pressure and density response curves of the flow conduit that intersect zero at a given working point, thereby rendering the flow conduit substantially insensitive to the pressure and density at the working point and (3) a detector circuit for measuring the altered vibration at the working point and producing a signal representing a mass flow rate that, by virtue of the intersection, is rendered substantially independent of effects of the pressure and density.

The second embodiment involves construction of a flow meter geometry that may not by itself be inherently insensitive to changing fluid properties, but with the application of a unique mathematical algorithm to the uncompensated flow signals derived from the device, the resultant signals are thereby rendered insensitive to changing fluid properties. In this second embodiment, the meter comprises: (1) a flow conduit for containing a fluid having a physical characteristic, the fluid adapted to flow in the conduit at an unknown rate, (2) a drive circuit for creating a vibration in the flow conduit, the fluid altering the vibration as a function of the physical characteristic and the flow rate, (3) a detector circuit for measuring the altered vibration at a working point and producing a signal representing an uncompensated mass flow rate of the fluid and (4) a computation circuit for calculating a compensated mass flow rate of the fluid proportional to the uncompensated rate by $1/\Omega 1^n$, where $\Omega 1$ is a driven natural frequency of the flow conduit and n is a number (either positive or negative) chosen as a function of the working point, the compensated rate thereby reduced of effects of the physical characteristic.

Alternatively, the meter can comprise: (1) a flow conduit for containing a fluid having a pressure and density, the fluid adapted to flow in the conduit at an unknown rate, the flow conduit composed of a desired material and having a desired length, radius and wall thickness, (2) a drive circuit for creating a vibration in the flow conduit, the fluid altering the vibration as a function of the flow rate, the desired material, length, radius and wall thickness yielding a response curve of the flow conduit that intersects zero at a given working point, the response curve selected from the group consisting of pressure and density, thereby rendering the flow conduit substantially insensitive to one of pressure and density at the working point, (3) a detector circuit for measuring the altered vibration at the working point and producing a signal representing a partially compensated mass flow rate that, by virtue of the intersection, is rendered substantially independent of effects of the one of pressure and density and (4) a computation circuit for calculating a compensated mass flow rate of the fluid proportional to the partially compensated rate by $1/\Omega 1^n$, where $\Omega 1$ is a driven natural frequency of the flow conduit and n is a number (either positive or negative) chosen as a function of the working point, the compensated rate thereby reduced of effects of both the pressure and density.

The present invention further contemplates a method of determining pressure and density with a Coriolis mass flow meter, involving the use of an arbitrary flow meter geometry and using two natural modes of vibration on the meter. This method of the present invention then calls for the simultaneous solution and compensation for both pressure and density effects. The method of determining pressure and density comprises the steps of: (1) providing a flow conduit for containing a fluid having a pressure and a density, the flow conduit composed of a desired material and having a desired length, radius and wall thickness, (2) causing the fluid to flow in the conduit at a given rate, (3) simultaneously creating two natural modes of vibration in the flow conduit with a drive circuit, the fluid altering the modes of vibration as a function of the pressure, density, flow rate, material, length, radius and wall thickness, (4) measuring the altered modes of vibration with a detector circuit at a working point, the detector circuit producing a first signal representing an uncompensated mass flow rate of the fluid, (5) changing the pressure and density of the fluid, (6) again measuring the altered modes of vibration with a detector circuit at the working point, the detector circuit producing a second signal representing an uncompensated mass flow rate of the fluid, (7) calculating the pressure and density by simultaneous solution, the simultaneous solution further providing a compensation factor relating to the material, length, radius and wall thickness of the flow conduit and (8) providing a computation circuit for the meter embodying the compensation factor.

Each of these methods of applying the current invention have their own advantages as hereinafter discussed.

Briefly, the present invention is directed to a Coriolis mass flow meter that is made to be insensitive to pressure, density, conduit stress or temperature, by virtue of its geometry and motion detection method or its geometry and motion detection method in combination with a mathematical algorithm or its geometry and motion detection method in combination with direct calculation of and compensation for the pressure and density of the fluid.

Several embodiments are disclosed that incorporate the desired insensitivity properties but vary in the complexity of either the sensor (forming a mechanical portion of the device) or the electronics (forming a signal processing portion of the device), since there is a natural tradeoff between the two.

As previously mentioned, the resulting flow-related deflection is usually a sinusoidal function of time, thereby causing a velocity, acceleration and a time delay also to be associated with the motion, all of which can be measured using fundamental sensing techniques (accelerometers, velocity sensors, displacement sensors, etc.). As a fortuitous consequence of nature, the measured response of a given conduit geometry to changes in fluid parameters (pressure, density, etc.) varies depending on which motion sensing technique is used. Furthermore, since there is a definite mathematical relationship between acceleration, velocity, displacement and time delay, a continuous characteristic curve can be defined describing the change in the response of the device to pressure, density, etc., as a function of sensing technique. The shape and zero intercepts of these characteristic curves for changes in pressure, density, temperature and conduit stress, can be effectively controlled according to the present invention, allowing the designer to choose the desired response to the extent that a sensor can be designed that is inherently insensitive to changes in these parameters.

In addition, an algorithm can be derived from these characteristic curves that can be advantageously applied to allow the designer to work at any desired point (defined for purposes of the present invention as a "working point") along the response curve. This aspect of the invention allows the designer to use sensor geometries that are not inherently insensitive to changes in fluid parameters and by applying the appropriate algorithm of the present invention, render its resulting flow-related signals insensitive to changes in fluid parameters.

Another embodiment of the invention is disclosed whereby a second mode of vibration is excited to determine its natural frequency. Due to a fortuitous relationship between pressure and density and the frequency of these two modes of vibration, a simultaneous solution of both the pressure and the density of the fluid can be attained. Knowing the value of both pressure and density in conjunction with the characteristic curves just described, a compensation value can be directly determined and accurately applied thereby rendering the resulting flow-related signals to be insensitive to changes in fluid parameters.

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art should appreciate that they may readily use the conception and the specific embodiment disclosed as a basis for modifying or designing other structures for carrying out the same purposes of the present invention. Those skilled in the art should also realize that such equivalent constructions do not depart from the spirit and scope of the invention as set forth in the appended claims.

BRIEF DESCRIPTION OF THE DRAWINGS

For a more complete understanding of the present invention and the advantages thereof, reference is now made to the following descriptions taken in conjunction with the accompanying drawings, in which.

DETAILED DESCRIPTION

Figure 1:
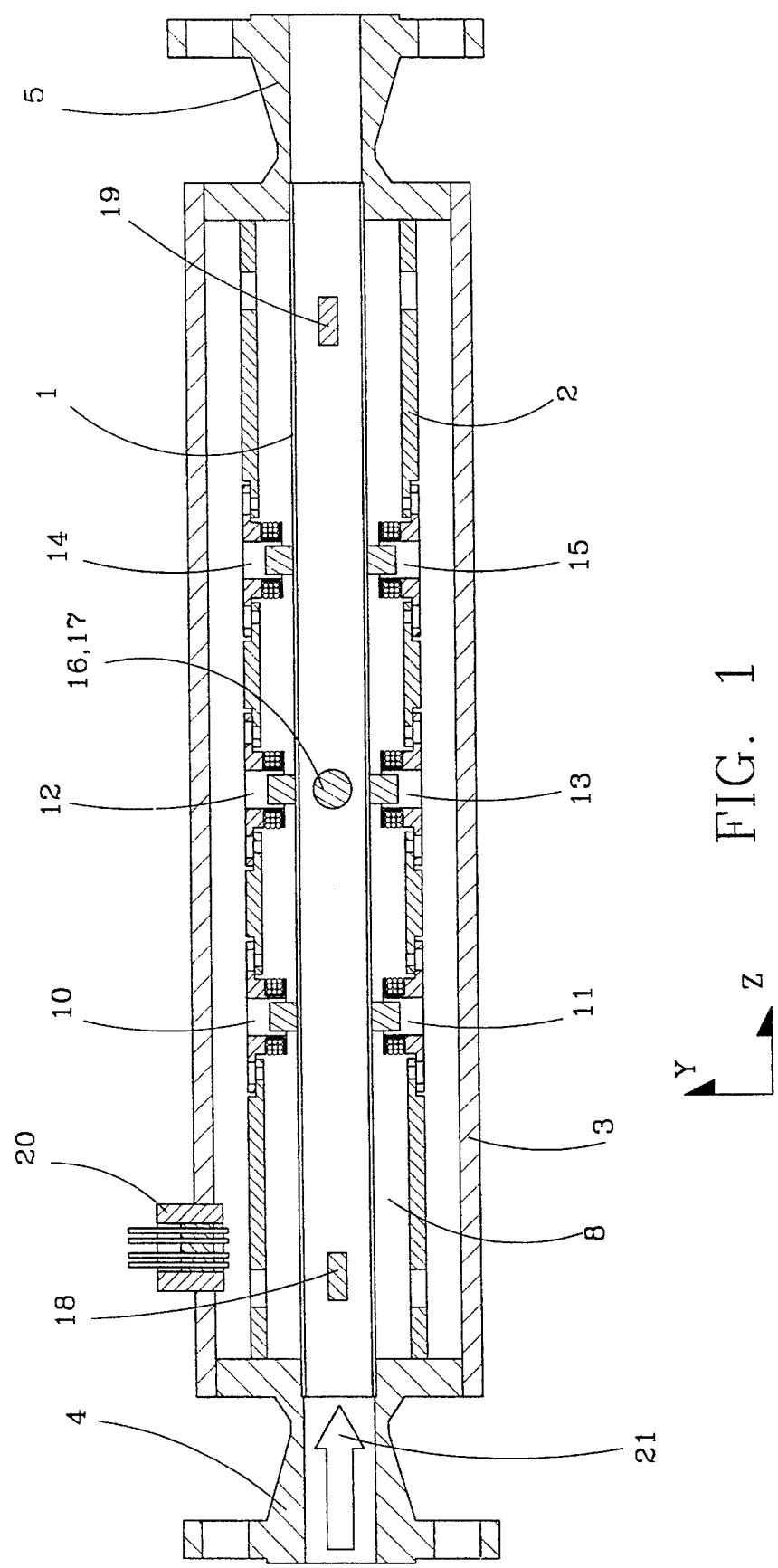
FIG. 1 illustrates a cutaway side view of a mechanical portion of a Coriolis mass flow meter device of the present invention.

FIG. 1 is illustrative of the mechanical portion (a sensor) of the present invention and will be used to describe several embodiment of the invention. The sensor consists of a single straight flow conduit 1 that is made of a strong resilient material such as 316 stainless steel or titanium. The flow conduit 1 is fixedly attached at both ends to manifolds 4, 5 by a welding or brazing process so that fluid flow 21 can easily pass into, through and out of the flow conduit 1 without leaking. Mounted in association with the flow conduit 1 is a support bracket 2 that is used to mount coils of magnet/coil pairs 10 through 17, support any requisite wiring and convey pipeline stress around the flow conduit 1, among other purposes. The support bracket 2 is preferably made of a strong material such as steel pipe and is preferably attached at its ends to the manifolds 4, 5 by a welding or brazing process.

Mounted in association with the support bracket 2 and the flow conduit 1 are magnet/coil pairs 10 through 17. The magnets of the magnet/coil pairs 10 through 17 are fixedly attached to the flow conduit 1 by a brazing process, although any suitable attachment method can be employed, such as adhesives or fasteners. The coils of the magnet/coil pairs 10 through 17 are fixedly attached to the support bracket 2 by suitable fastening hardware. The magnet/coil pairs 10 through 15 are used as motion detectors and being magnets and coils, will detect the velocity of relative motion between each magnet and its associated coil. This velocity will appear as a voltage on the coil wires proportional in magnitude to this relative velocity. The magnet/coil pairs 16, 17 are used as drivers to excite the flow conduit 1 to vibrate in a prescribed mode of vibration.

Also mounted in association with the flow conduit 1 are a strain gage 19 and a temperature sensor 18. The strain gage 19 is preferably a semiconductor type or metal film type strain gage mounted on a polyimide backing material and arranged to sense the axial (in the direction of flow 21) strain in the flow conduit 1 due to temperature or pipeline induced axial strains. The temperature sensor 18 is preferably a 100Ω platinum resistance thermal device ("RTD"), mounted to the flow conduit 1 by means of thermally conductive adhesive and arranged to accurately sense the temperature of the flow conduit 1.

Concentrically mounted around the support bracket 2 and the flow conduit 1 is a pressure tight case 3 that is preferably fixedly attached at its ends by welding or brazing to the manifolds 4, 5 so that an annular space 8 is enclosed between the flow conduit 1 and the case 3, that can be held at a vacuum or a predetermined amount of pressure. The case 3 is preferably round and made of a strong material such as steel pipe or tubing capable of withstanding internal pressures or vacuums and capable of withstanding pipeline forces and stresses.

Mounted in association with the case 3 is a feed through 20 that is used to convey signals through the pressure tight case 3 while maintaining a vacuum or predetermined pressure in the annular space 8. Preferably, the feed through 20 is made of steel, is attached to the case 3 by a welding or brazing process and incorporates glass to metal seals for each individual signal carrier to maintain the annular space 8 at a vacuum or predetermined pressure without leaking.

FIG. 1, as just described, is therefore a representative Coriolis mass flow sensor geometry that will be used to further describe the aforementioned characteristic response curves to changes in pressure, density, temperature and conduit stress, the control of these characteristic response curves to achieve insensitivity to these parameters and the mathematical algorithm derived from these curves that can be advantageously applied to effect insensitivity to these parameters. It is important to note, however, that the methods described herein to control these characteristic response curves and the algorithms later defined, apply to a wide variety of Coriolis mass flow sensor geometries including traditional bending mode meters, as well. The geometry of FIG. 1 is, however, the preferred sensor geometry.

Figure 9:
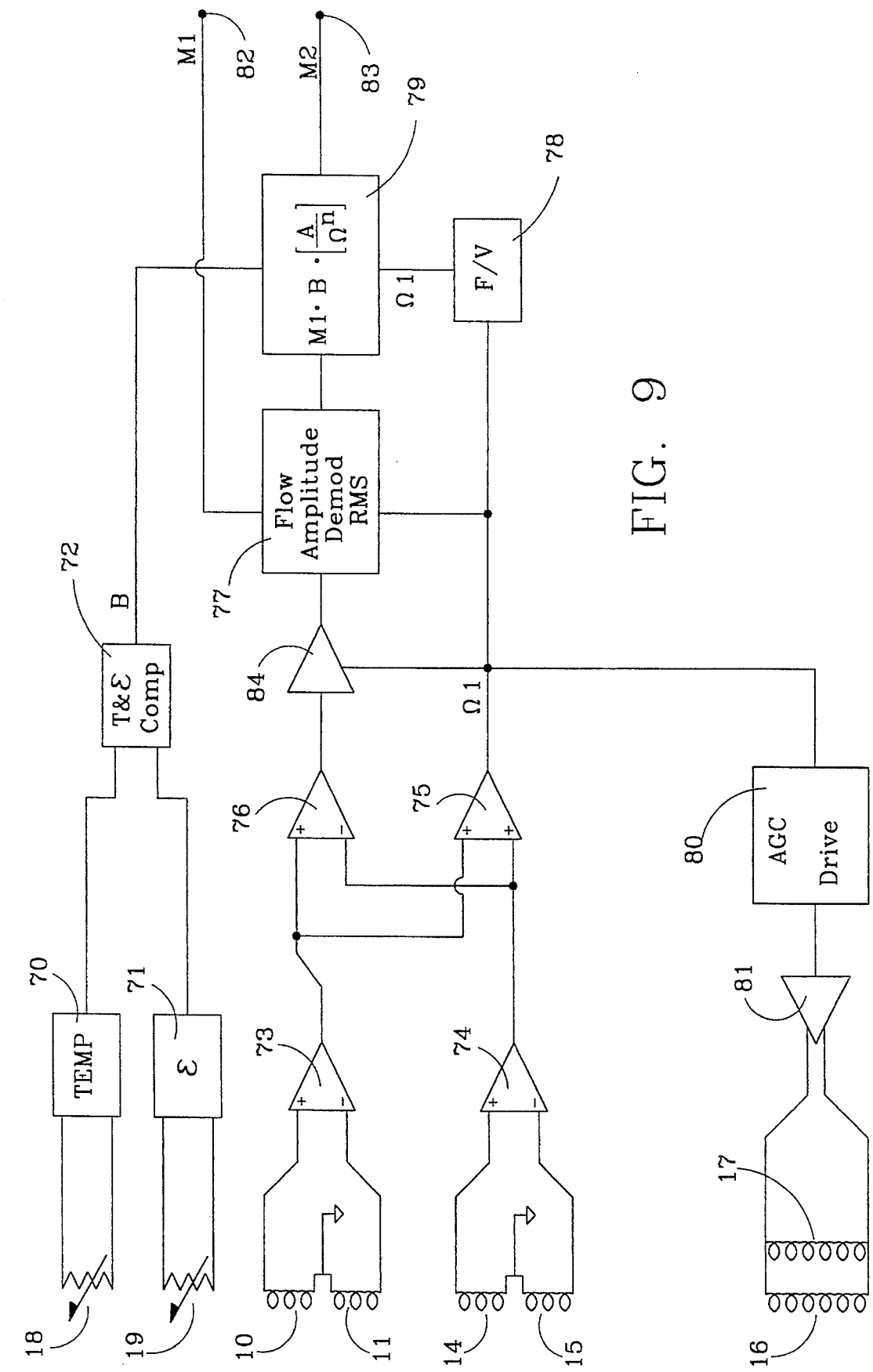
FIG. 9 illustrates an exemplary circuit diagram for processing the signals of the present invention.

FIG. 9 is representative of an electronic circuit that can be used in conjunction with the sensor of FIG. 1 to excite the requisite oscillatory vibration on the flow conduit 1 and to extract from the resulting motion, signals that are proportional to the mass flow rate of the fluid flow 21.

Figure 2:
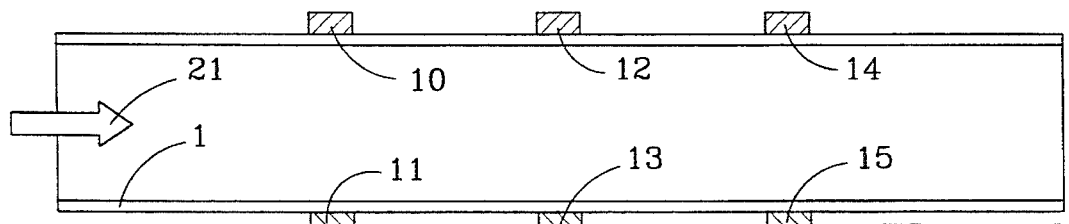
FIG. 2 illustrates a side view of a vibrating portion of the Coriolis mass flow meter device of FIG. 1 shown in its undeflected position.
Figure 3:
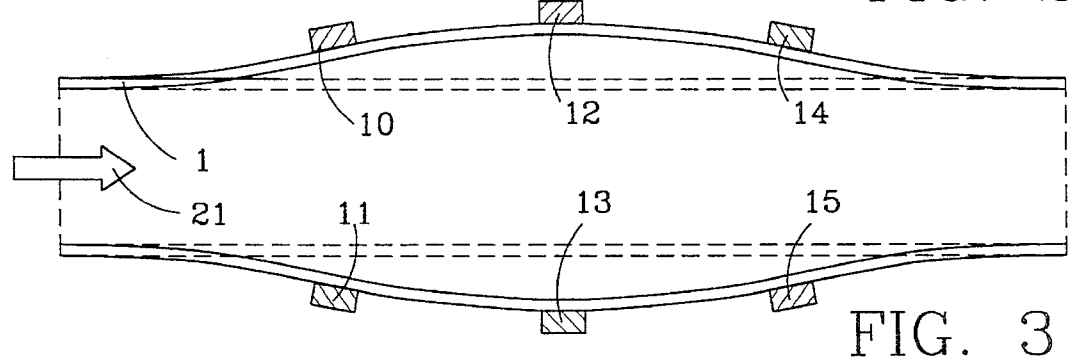
FIG. 3 illustrates a side view of a vibrating portion of the Coriolis mass flow meter device of FIG. 1 shown in a deflected position representing a first elliptical radial mode.

Since the sensor of FIG. 1 is designed to be a highly resonant structure, it will normally have the ability to vibrate in several natural modes of vibration. FIGS. 2 through 6 depict a progression of natural mode shapes that can be excited on the flow conduit 1. FIG. 2 shows the flow conduit 1 in its undeflected position. FIG. 3 shows a first elliptical radial mode where the term "first" describes the progression of complexity of the mode as it pertains to the number of waves above or below the undeflected position, along the length of the flow conduit 1. For these examples, it is assumed that the cross-sectional shape of the deflected conduit is elliptical, however there is a similar progression in complexity of the natural modes pertaining to the cross-section as well, from elliptical to triangular to rectangular, and so forth for geometries of higher complexity. Assuming the cross-sectional deflected shape to be elliptical, FIG. 4 therefore represents a second elliptical radial mode, FIG. 5 represents a third elliptical radial mode and FIG. 6 represents a fourth elliptical radial mode.

Figure 4:
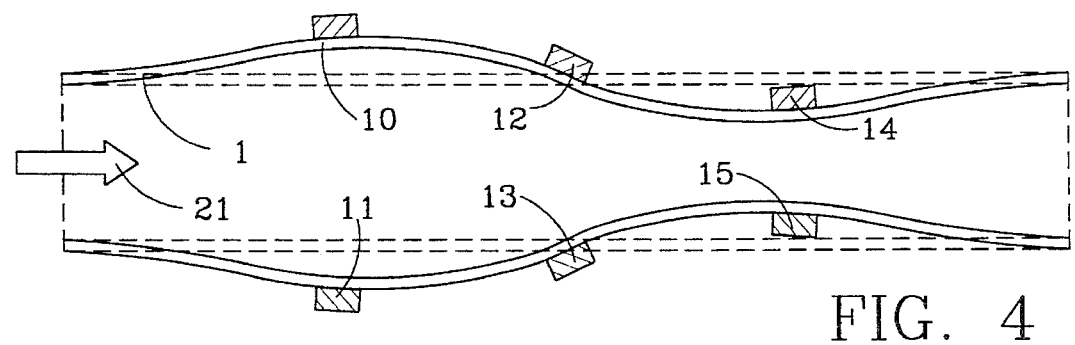
FIG. 4 illustrates a side view of the vibrating portion of the Coriolis mass flow meter device of FIG. 1 shown in a deflected position representing a second elliptical radial mode.
Figure 5:
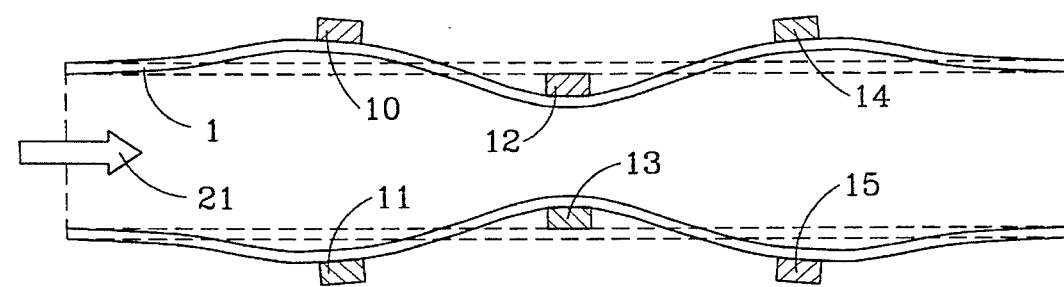
FIG. 5 illustrates a side view of the vibrating portion of the Coriolis mass flow meter device of FIG. 1 shown in a deflected position representing a third elliptical radial mode.
Figure 6:
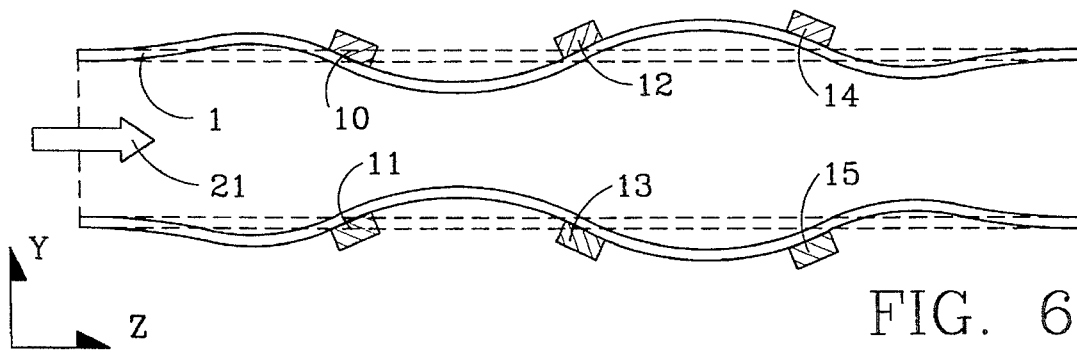
FIG. 6 illustrates a side view of the vibrating portion of the Coriolis mass flow meter device of FIG. 1 shown in a deflected position representing a fourth elliptical radial mode.

Any of the depicted mode shapes of FIGS. 3 through 6 and others not shown can be selected as the desired driven mode of vibration to cause the requisite Coriolis forces. In general, the resultant shape of the Coriolis force distribution, and thus the flow-related deflected shape of the conduit, will be similar to the next higher mode shape above the chosen driven mode shape. For example, for the preferred embodiment, the first elliptical radial mode is chosen as the desired driven mode of vibration as shown in FIG. 3. The combination of the fluid flow 21 and conduit motion in the shape of the flow conduit 1 in FIG. 3 cause a Coriolis force distribution and resulting conduit wall deflection that is similar in shape to the second elliptical radial mode as shown in FIG. 4. Similarly, if the third elliptical radial mode of FIGURE 5 is chosen to be the driven mode of vibration, the resulting Coriolis force distribution and resulting deflected conduit shape will be similar to that of the fourth elliptical radial mode as shown in FIG. 6.

For a given conduit geometry, the magnitude of the flow induced deflection, as seen by the motion sensors 10 through 15, is dependent on the mass flow rate and the frequency response of the conduit at the location of the motion sensors. Unfortunately, this frequency response is itself dependent on other factors (response variables) including (a) the state of stress in the conduit from, for example, fluid pressure, end loading and gravity, (b) the elastic modulus of the conduit material (primarily a function of the materials temperature), (c) the density of the fluid in the conduit and (d) fluid viscosity. In addition, this frequency response is also dependent upon what type of motion detection method is used, i.e. velocity (as in the preferred embodiment), acceleration, displacement or time delay.

It is the control of frequency response through specific geometric design or subsequent compensation (through either the application of a specific mathematical algorithm or direct determination of the response variables or coefficients), that achieves the desired goal of insensitivity to these response variables. This is a central goal of the present invention.

Four embodiments are disclosed that incorporate the desired insensitivity properties but vary in the complexity of either the sensor (mechanical portion of the device) or the electronics (signal processing portion of the device), since there is a natural tradeoff between the two.

Figure 7:
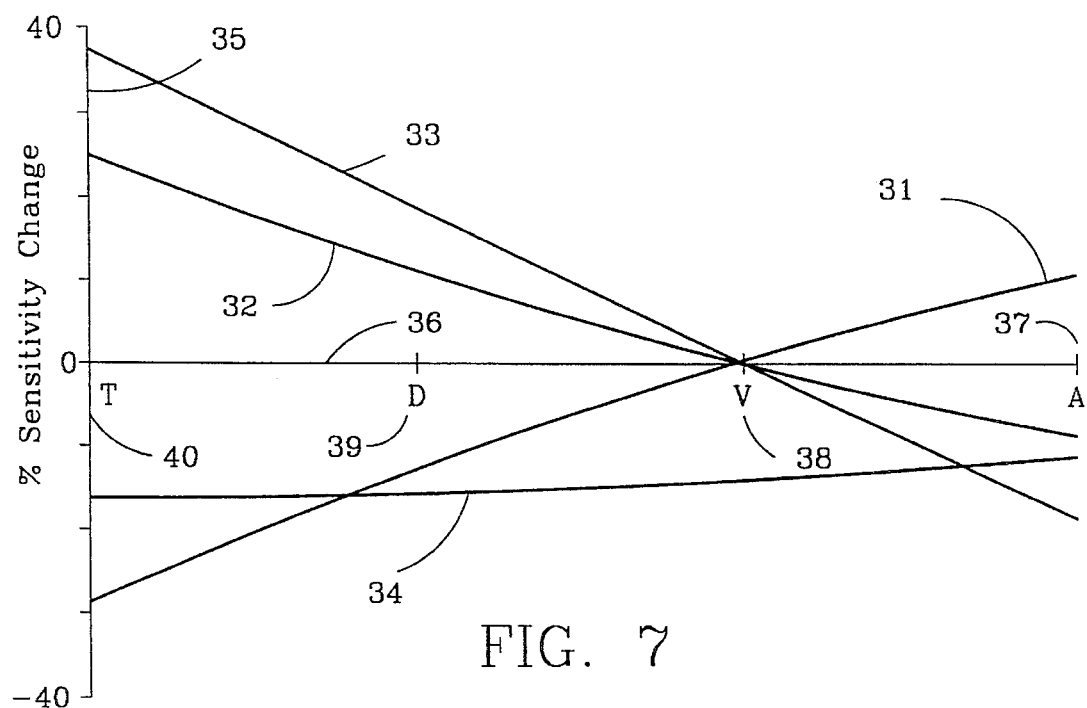
FIG. 7 illustrates a graph of curves representing a change in sensitivity of the Coriolis mass flow meter device of FIG. 1 to changes in pressure, temperature, axial stress and density, where some of the curves intersect each other at a zero value and at a working point corresponding to a fundamental measurement method.

The first embodiment to be discussed involves the most complex sensor geometry but the simplest signal processing necessary to achieve the desired results. Referring to FIG. 7, the characteristic response curves 31 through 34 for the conduit geometry of FIG. 1 are plotted in graphical format. These response curves are calculated using finite element analysis ("FEA") methods to determine the change in the response of a particular sensor design to changes in fluid pressure, density or conduit elasticity, among other factors.

A horizontal axis 36 of FIG. 7 is essentially the progression of motion detection methods used to sense the Coriolis-induced conduit deflections starting with a time delay measurement 40 at the left, going through a displacement measurement 39, a velocity measurement 38 and an acceleration measurement 37 at the right end. Since the Coriolis-induced motion is a sinusoidal function of time, each successive measurement method along the horizontal axis 36 is mathematically related to the next by an integral (or differential) function of time and can be represented by integer multiples of the natural driven frequency of the conduit. For example, if accelerometers are used as the primary motion sensors on the conduit, integrating the acceleration-related output signals with respect to time or dividing the magnitude of these signals by the natural frequency $\Omega 1$ of the conduit results in signals proportional in magnitude to the velocity of the conduit. Thus, velocity sensors instead of accelerometers can be used directly (as in the preferred embodiment). Similarly, integrating or dividing velocity signals by the natural frequency $\Omega 1$ results in signals proportional to the displacement of the conduit. Thus, displacement sensors instead of velocity sensors can be used directly. Dividing displacement signals by the natural frequency $\Omega 1$ results in signals proportional to the time delay of the conduit. Alternately time delay, rather than displacement, can be sensed directly. This has been the traditional method of choice.

A vertical axis 35 of FIG. 7 represents the change in the sensitivity of the device due to a given change in one of the response variables (i.e. pressure, temperature, density or stress). Accordingly, the pressure response curve 31 shows that, with a given increase in fluid pressure (for example, increasing from 0 to 1000 psi), there is a positive increase in the sensitivity change of the device from left to right along the horizontal axis 36. Specifically, if time delay methods are used to measure the Coriolis-induced motion of the conduit, the working point along the horizontal axis 36 will be at a far left end 40 and, as pressure increases, according to the curve 31 the sensitivity of the device will decrease (about −28% for the prescribed 1000 psi increase for this example).

If displacement sensors are used to measure the motion, the working point along the horizontal axis 36 will be at the working point 39 where increases in pressure still cause a corresponding decrease in the sensitivity of the device, however not as much as if time delay methods had been used. Fortuitously, the pressure response curve 31 actually intersects a zero value at the working point 38 corresponding to the velocity of the conduit. Therefore, if velocity sensors are used as in the preferred embodiment, there will be no change in the sensitivity of the device with changes in fluid pressure. Finally, if accelerometers are used, the working point along the horizontal axis 36 will be at the working point 37 resulting in an increase in sensitivity of the device with increases in fluid pressure.

The density response curve 32 is similar to that just described for pressure, except it depicts the change in the sensitivity of the device due to a given increase in the fluid density, for example increasing from the density of ambient air in the conduit to that of water. In general, the density response curves slopes in a direction opposite to that of the pressure response curves, thereby showing a decrease in sensitivity change as the working point moves from left to right along the horizontal axis 36.

Again, if velocity sensors are used as the measurement method, there will be no change in the sensitivity of the device with changes in the fluid density. This fortuitous condition of having both the pressure and density response curves 31, 32 intersect a zero value at the same working point along the horizontal axis 36 and furthermore to have an intersecting working point 38 coincide with a fundamental measurement method such as velocity, is, of course, the desired result and is herein achieved by controlling the sensor geometric design parameters of flow conduit length, wall thickness, elastic modulus and the magnitude and location of individual masses such as the magnets used for both sensing and driving the conduit motion.

The control of the slope and the intercepts of the pressure and density response curves 31, 32 due to changes in specific geometric design parameters is hereinafter discussed in detail to allow the designer control over these characteristic curves.

The temperature response curve 33 of FIG. 7 is shown sloping down toward the right indicating that an increase in the temperature (and thus a decrease in the elastic modulus) has a corresponding effect on the sensitivity of the device depending on which type of measurement method is used. The temperature response curve 33 intersects a zero value at the working point 38, corresponding to the velocity measurement method. Accordingly, if velocity measurement methods are used, changes in the elastic modulus due to temperature, will have little or no effect on the sensitivity of the device. In general, the shape of the temperature response curve 33 is less affected than are the pressure curve 31 or the density curve 32 by varying geometric design parameters. Since temperature is easily measured and compensated for using simple electronic methods, the control of the shape and intercept of the temperature response curve 33 is usually not necessary.

The stress response curve 34 of FIG. 7 depicts the response of the device with an increase in axial tensile stress in the flow conduit of, for example, 20,000 psi. The stress response curve 34 accordingly shows that increases in axial tensile stress in the conduit result in a negative change in the sensitivity of the device, regardless of the type of detection method used. In general, the stress response curve 34 will not intersect a zero value within reasonable limits of design geometry. However, since axial tensile stress is easily eliminated by incorporating a bellows or slip joint arrangement in the conduit or measured using a strain gage, control of the shape and intercept of the axial stress response curve is usually not necessary.

Therefore, for this example, a geometry is thus created that, by using velocity sensors, is unaffected by changes in pressure, density and temperature, simply by virtue of its geometry and motion detection method. Axial stress effects can also be eliminated by encompassing a bellows or slip joint arrangement onto the flow conduit, thereby making the device insensitive to all response variables except mass flow rate. An example of a set of geometric design parameters that meet this criteria are as follows:

Flow Conduit Diameter: 1"
Flow Conduit Length: 12"
Flow Conduit Wall: 0.049"
Flow Conduit Metal: 316 SS (Elastic Modulus=29e6)
Drive Masses (2): 0.185 oz. (FIG. 1, items 16 and 17)
Sensor Masses (4): 0.041 oz. (FIG. 1, items 10, 11, 14 and 15)
Sensor Mass Locations: 25% & 75% of Conduit Length, Diametrically opposed To use the geometry of this first embodiment, the sensor of FIG. 1 is used in combination with the circuit of FIG. 9, as follows. The requisite driven motion of flow conduit 1 is excited by the application of electrical signals of the appropriate phase and amplitude from a circuit component 81 into drive coils 16, 17 that are appropriately connected so that the resulting force causes the desired radial vibration, such as the first elliptical radial mode of FIG. 3. For maximum efficiency, the current supplied to coils 16, 17 is in phase with the desired velocity of the conduit motion. Once the desired vibratory motion is achieved, it is maintained at a constant level via an automatic gain control ("AGC") drive 80.

With the driven motion established, signals from the diametrically opposed magnet/coil pairs 10, 11 near the inlet of the flow conduit 1 are summed together in a differential operational amplifier ("op-amp") 73 to yield signals proportional to radial motions and to eliminate signals proportional to common (bending mode) motion. Similarly, signals from the magnet/coil pairs 14, 15 near the outlet of the flow conduit 1 are summed together in a differential op-amp 74 to yield signals proportional to radial motions and to eliminate signals proportional to common (bending mode) motion. These resulting signals are then applied to both a summing op-amp 75 and a differential op-amp 76 to separate in-phase and out-of-phase components. The output of the summing op-amp 75 is a sine wave proportional in amplitude to the driven velocity of the flow conduit 1 at the magnet/coil pair 10, 11, 14, 15 locations. Similarly, the output of the differential op-amp 76 is a sine wave proportional in amplitude to the velocity of the induced Coriolis deflections at those same locations. Since the Coriolis-induced velocity will normally be a small percentage of the driven velocity, and since the in-phase portion of the signals from the differential op-amps 73, 74 may not match precisely in amplitude, the resulting difference from the differential op-amp 76 may contain a remnant amount of the in-phase component. This remnant value may be neglected if it remains constant over variations in operating conditions, or it may be subtracted by summing a countervailing, equivalent negative amount of the in-phase component through a component 84. A demodulator 77 therefore receives input from the component 84 and determines the root mean square ("RMS") voltage or average voltage value of this sine wave using common techniques such as rectification, peak detection, asynchronous or synchronous demodulation. To maximize noise immunity, a synchronous demodulation technique using the driven frequency as the demodulation reference is the preferred technique.

If the strict geometric design parameters as just described are adhered to and if axial stress is held to be negligible, no further compensation is required for this signal, since as previously described, it will not vary with pressure, density or temperature variations. The demodulator 77 therefore can provide an output signal (M1) 82 that is proportional to the mass flow rate and insensitive to these other variables. This represents the first embodiment that imposes the most stringent requirements on geometric design but has the simplest signal processing circuitry.

Because of normal material and manufacturing variations, the response curves 31 through 33 may not intersect perfectly as shown on FIG. 7. As will be discussed later in detail, these response curves can be controlled by design. However, after a sensor has been manufactured and found to be slightly "off" due to these variations, a final correction can be made during a subsequent calibration procedure. To effect this correction, the sensor is flow-tested at two different pressures and densities to determine the slope and intercept of the response curves. With this information, additional masses can easily be added at appropriate points along the length of the flow conduit 1 to shift the response curves back to the correct intercepts.

The geometric design requirements of this first embodiment may impose restrictions upon the designer that are undesirable. As a practical matter, there are many possible sensor attributes that a designer may want to optimize for a particular design. Among these are pressure drop with flow, sensitivity, natural frequency, safety and corrosion resistance. Each of these can be effected by geometric design parameters and it is therefore desirable to allow the designer as much freedom as possible to optimize the most important attribute for a given design.

The second embodiment of the present invention, that is a preferred embodiment, therefore addresses this problem and allows the designer more freedom to optimize geometric design parameters such as flow conduit length, wall thickness and magnet size and location, without the restriction of having the pressure and density response curves 31, 32, intersect at a primary measurement method such as velocity 38.

As an example of a sensor geometry for the second embodiment the following design parameters are representative:

Flow Conduit Diameter: 1"
Flow Conduit Length: 10"
Flow Conduit Wall: 0.028"
Flow Conduit Metal: 316 SS (Elastic Modulus=29e6)
Drive Masses (2): 0.08 oz. each (FIG. 1, items 16 and 17)
Sensor Masses (6): 0.041 oz. each (FIG. 1, items 10 through 15)

Sensor Mass Locations: 25%, 50% & 75% of Conduit Length, Diametrically opposed

This second embodiment is therefore shorter, has thinner walls and lighter drive masses than the first embodiment, which may be desirable to optimize some of the aforementioned sensor attributes such as pressure loss and sensitivity.

Figure 8:
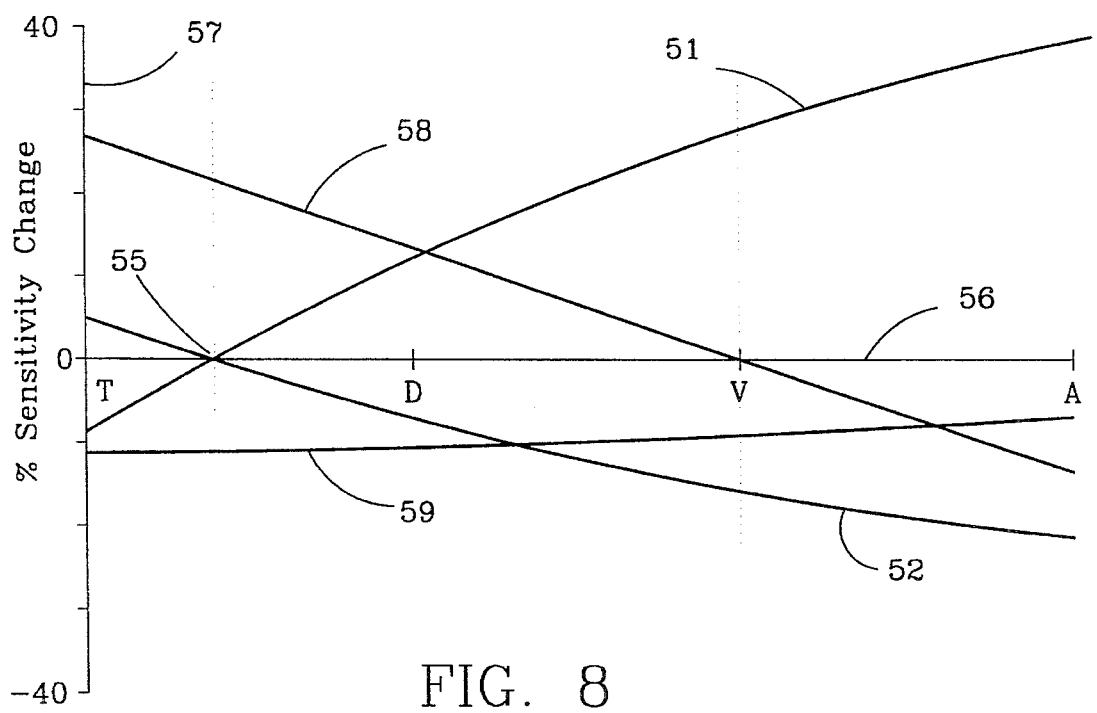
FIG. 8 illustrates a graph of curves representing a change in sensitivity of the Coriolis mass flow meter device of FIG. 1 to changes in pressure, temperature, axial stress and density, where some of the curves intersect each other at a zero value, but not at a working point corresponding to a fundamental measurement method.

Referring to FIG. 8, pressure and density response curves 51, 52 are representative of the response characteristics of this second embodiment. These curves indicate similar shape and slopes to those of the first embodiment (the curves 31, 32 of FIG. 7), however, the significant difference is that their zero value intercepts 55 occur at a working point along an horizontal axis 56 that does not coincide with a primary measurement method. However, due to the mathematical relationship between the measurement methods as earlier described, it is not necessary to achieve coincidence with a measurement method. No matter the type of measurement method chosen for the primary motion sensing, the resulting signals can be mathematically transformed to any arbitrary working point along the horizontal axis 56 by applying to the resulting flow-related signals, a function proportional to $\Omega^n$, where $\Omega$ is the driven natural frequency of the conduit at the time the flow signals are attained and n is the exponential number (either positive or negative) necessary to achieve the desired transformation. In this example, velocity signals were the chosen measurement method using a common magnet and coil arrangement to derive signals proportional to the velocity of the Coriolis-induced motion.

Dividing the magnitude of these velocity signals by $\Omega^1$ equates to using displacement sensors and reduces the pressure and density sensitivity by the amount shown on the pressure and density response curves 51, 52, however this does not eliminate the problem. Dividing these velocity signals by $\Omega^2$ equates to using time delay measurement and, for this example, reduces the pressure and density effects (and reverses their polarities) but, again, does not eliminate them.

The use of integer real values (either positive or negative) for the exponential number n functionally transforms the fundamental sensor signals from one fundamental type (velocity) to another (displacement, etc.). While commercially-available transducers are usually restricted to these fundamental types corresponding to integer real values of n, the exponent number in the algorithm is not restricted to integer real values and, indeed, the correct function for this geometry is to divide the magnitude of the flow-related velocity signals by $\Omega^{1.6}$ (a noninteger number for n). This renders the resulting flow signals insensitive to both pressure and density at the same time. Physically, this equates to using a hypothetical sensor providing signals proportional to a blend of 60% time delay and 40% displacement. This can actually be achieved by using these two methods and blending their signals in the correct proportions or by using displacement sensors and applying a partial integration of the signal. However, these methods are analogous and tend to add unnecessary complexity to the simple method described herein for the preferred embodiment.

A temperature response curve 58 and an axial stress response curve 59 are similar to the corresponding temperature and axial stress response curves 33, 34 of FIG. 7 of the first embodiment. These curves 58, 59 were effectively unchanged by the geometric difference between the first and second embodiments. By dividing the flow-induced velocity signals (M1 from the demodulator 77 of FIG. 9) by $\Omega^{1.6}$, the effective working point along axis 56 of FIG. 8 is transferred from velocity to an intercept working point 55 that eliminates the effects of both pressure and density. However, unlike the first embodiment, it creates a sensitivity to temperature, as can be seen by the positive value of the temperature response curve 58 above the intercept working point 55. Therefore, working at the working point 55, the sensitivity of the device increases with an increase in temperature. Similarly, the axial stress response curve 59 indicates that, at the working point 55, there will be a negative effect on the sensitivity of the device with an increase in axial stress.

To use the algorithm and compensate for both temperature and axial stress, the circuit of FIG. 9 incorporates all the components used for the first embodiment and further incorporates additional circuit components that were not used for the first embodiment.

To compensate for the effect of temperature, a temperature sensor 18 and a corresponding scaling component 70 are used to create a scaled compensation value appropriate for the chosen working point 55 along the horizontal axis 56 in combination with the temperature response curve 58. Similarly, if axial strain is not held to be negligible or constant, its value can be measured and compensated for via the strain gage 19 and a corresponding scaling component 71, used to create a scaled compensation value appropriate for the chosen working point 55 along the horizontal axis 56 in combination with the axial stress response curve 59. These compensation values from the scaling components 70, 71, can be summed and further scaled in the compensation component 72 and then applied to the computational component 79.

The computational component 79 receives an uncompensated mass flow rate signal (M1) from the demodulator 77, stress and temperature compensation values B from the compensation component 72 and the value of the driven frequency $\Omega 1$ from the component 78. These values are then combined within the computational component 79 to apply the following algorithm:

$$M2 = M1 * B * (A/\Omega 1^n) \quad (1)$$

Where:

M2=Final compensated flow rate signal;

M1=Uncompensated flow rate signal;

B=Temperature and strain compensation values;

A=Scaling, i.e. [0-pressure frequency(Hz)] /[0-pressure sensitivity(Volts/Flow Rate)];

$\Omega 1$=Driven natural frequency; and n=Exponent appropriate for the working point along axis 56 (1.6 for this example).

The resultant output signal (M2) 83 from the computational component 79 is therefore insensitive to pressure and density changes by virtue of the ($\Omega 1^n$) portion of the algorithm and is further insensitive to temperature and axial stress changes by virtue of the (B) portion of the algorithm. As a practical matter, the functionality of the computational component 79 can be implemented via analog components such as Burr Brown part number 4302, or Analog Devices part number AD538. Similarly, this functionality can easily be converted to a digital design with the algorithm being implemented as a sequence of computer instructional codes executable in a general purpose computer in a conventional manner.

Figure 10:
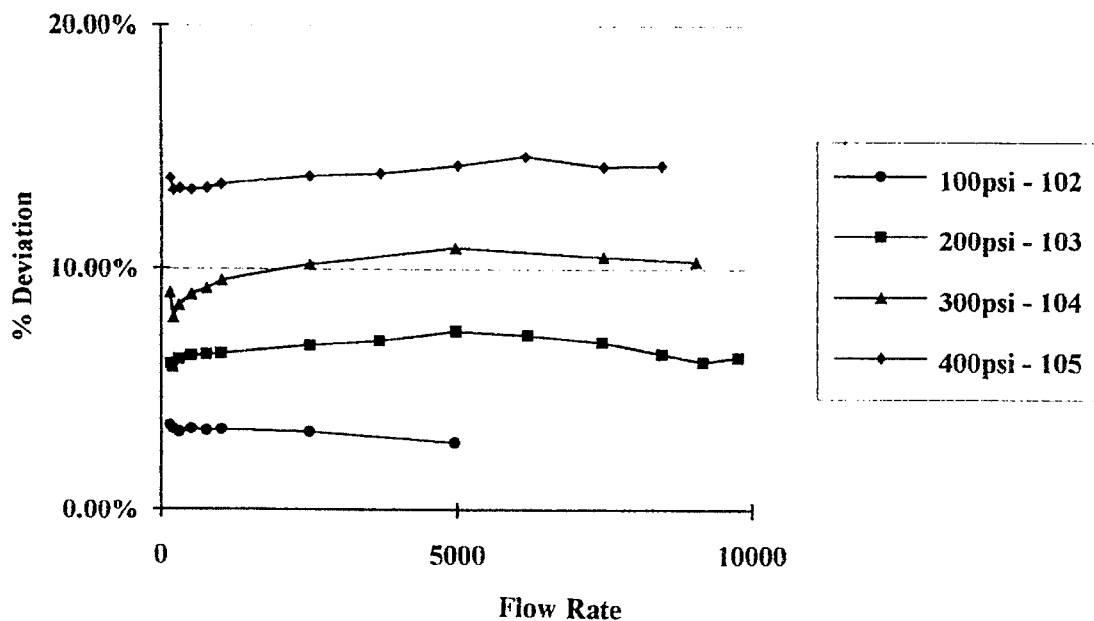
FIG. 10 illustrates a graph of actual data taken from a prototype Coriolis mass flow meter device of the present invention depicting a percentage deviation in accuracy of the device due to changing pressure.

FIG. 10 depicts uncompensated actual data from flow testing of a sensor designed according to this second embodiment. The horizontal axis represents the flow rate in pounds of air per hour and the vertical axis represents the percentage deviation from the reference meters. Data sets 102 through 105 represent the percentage deviation of the device from the reference meters, various flow rates and at 4 different pressures. The data set 102 was taken with air flow at 100 psi pressure. Similarly, the data sets 103, 104, 105 correspond to pressures of 200, 300 and 400 psi, respectively. These uncompensated data sets correspond to signal (M1) 82 of the circuit of FIG. 9. This corresponds to working at the velocity working point along the horizontal axis 56 of FIG. 8 that predicts the positive effect on sensitivity with increasing pressure as shown by the positive value of the pressure response curve 51 above the velocity working point. Therefore, as the pressure was increased for each data set, the meter sensitivity increased causing increasingly higher deviation values as seen in FIG. 10.

The temperature and axial stress values were held to be constant during the tests, eliminating a need to include compensation for these parameters in the algorithm. The following Table I represents the observed operating frequency of the tested device as a function of pressure. These frequency values were then incorporated into the algorithm with the results shown in FIG. 11.

TABLE I

| psi | Frequency (Hz) |
|---|---|
| 0 | 2951.2 |
| 100 | 3014.7 |
| 200 | 3075.2 |
| 300 | 3135.7 |
| 400 | 3196.3 |

Figure 11:
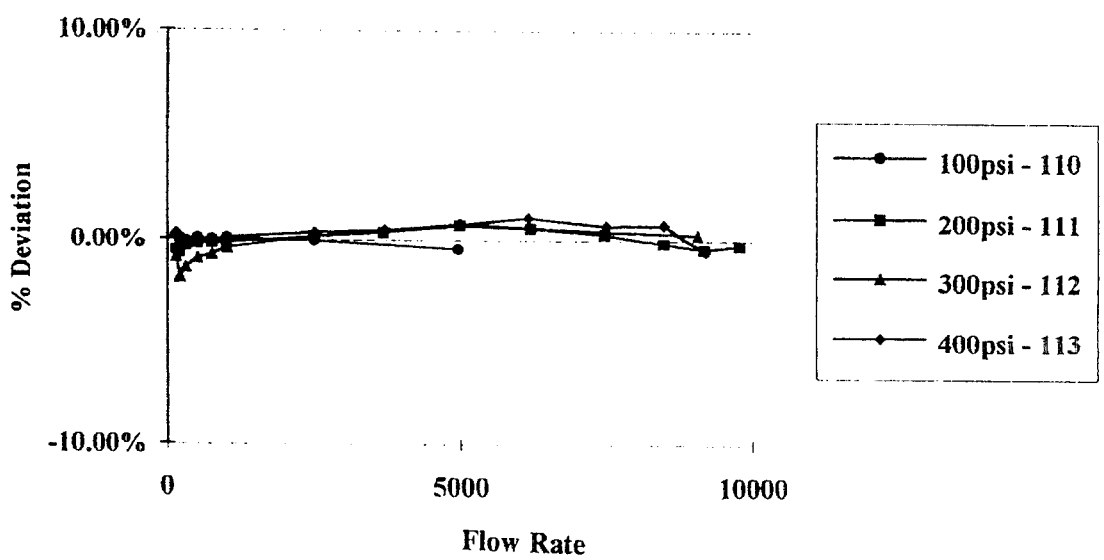
FIG. 11 illustrates a graph of actual data taken from a prototype Coriolis mass flow meter device of the present invention depicting the accuracy of the resulting mass flow rate calculations after using the algorithm described herein to compensate for pressure and density.

Data sets 110 through 113 of FIG. 11 therefore depict the percentage deviation with respect to the reference meters after the application of the algorithm and corresponds to the compensated output signal (M2) 83 of FIG. 9. FIG. 11 shows that the application of the algorithm, by virtue of the increasing frequency term in the denominator with increasing pressure, effectively offsets the increasing sensitivity of the velocity signals (M1) 82 by the exact amount necessary to render the final output signals (M2) 83 insensitive to both pressure and density changes.

This second example of the present invention therefore constitutes an embodiment that is inherently insensitive to both pressure, density, temperature and axial stress by virtue of its geometry in combination with a compensation algorithm. This embodiment has the tremendous advantage of allowing the designer a wide range of geometric freedom to maximize any desired performance attribute. However, this embodiment requires more sophisticated signal processing than does the first embodiment due to the application of the requisite algorithm.

Figure 12:
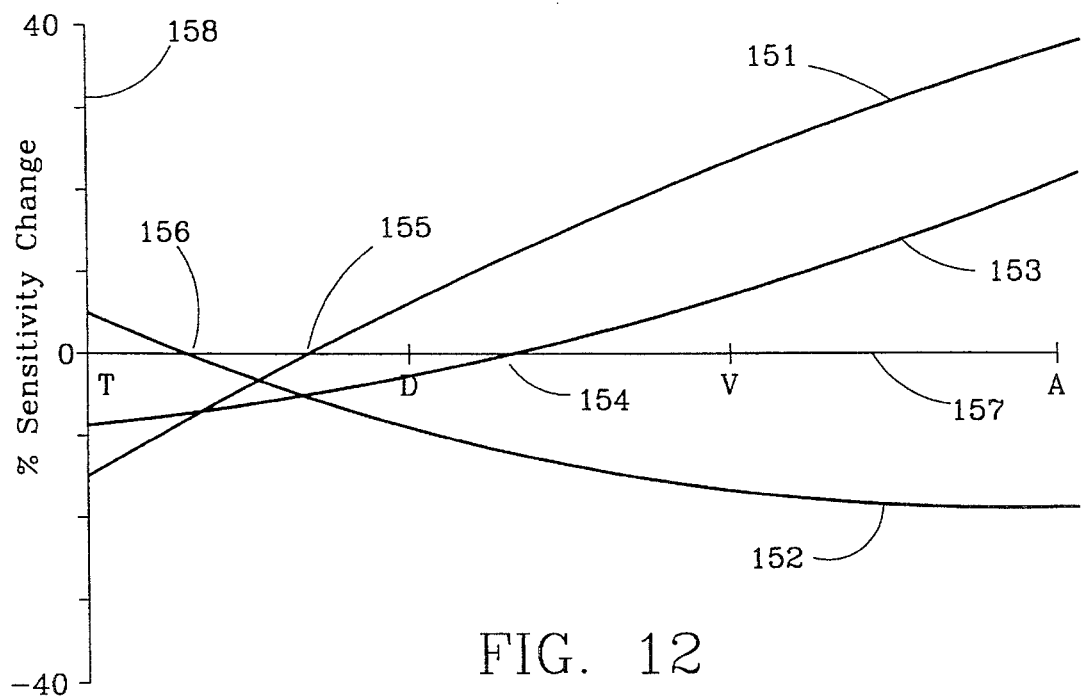
FIG. 12 illustrates a graph of curves representing a change in sensitivity of the Coriolis mass flow meter device of FIG. 1 to changes in pressure and density, where both curves intersect each other at a non-zero value.

A third embodiment of the present invention allows more geometric design freedom than the previous two embodiments without adding more complexity to the electronics. The tradeoff to this embodiment is that it is insensitive to pressure and density changes, but only for specific fluid properties, specifically fluids with a predictable relationship between their pressure and density. FIG. 12 depicts pressure and density response curves 151, 152, respectively, according to this third embodiment. By allowing the designer complete geometric freedom, sensor geometries can be created having pressure and density response curves 151, 152 that do not intersect zero values (155, 156) at the same working point along a horizontal axis 157. This situation allows the designer maximum geometric design freedom but presents the problem of how to compensate for changing response variables. As a practical matter, zero intercepts 155, 156 can generally be maintained acceptably close to one another for most sensor geometries by design. However, both geometric design parameters, as well as material and manufacturing anomalies, can alter the location of these intercepts and thereby cause them to be non coincident.

One solution to this problem according to the third embodiment is specific to the intended fluid to be measured. For example, if it is known that the fluid to be measured will not appreciably change density over the intended operating conditions, then the working point is chosen at the zero intercept 155 along the axis 157 and the appropriate value for the exponential number n is applied using the aforementioned algorithm. For this example, to move the working point from velocity to the working point zero intercept 155 requires a value for n of approximately 1.3. Similarly, if the application is known to be at constant pressure, then a working point should be chosen at the zero intercept 156 and the appropriate value for the exponential number n should be applied using the aforementioned algorithm. For this example, to move the working point from velocity to the zero intercept 156 requires an exponent value for n of approximately 1.7.

If there is a known relationship between the pressure and the density of the fluid to be measured, for example, by using the ideal gas equation for a gaseous fluid, then a third, net resultant response curve 153 can be plotted in FIG. 12 that is the net resultant response curve for the combined effect of both pressure and density for that particular fluid. To compensate for this net effective response curve 153, a working point 154 is used and the appropriate value for the exponential number n should be applied using the algorithm of equation (1). For this example, to move the working point along the axis 157 from velocity to working point 154 requires a value of approximately 0.6 for the exponential number n in equation (1). Since there may be a temperature dependence between the pressure and density of a given fluid, the temperature compensation value (not shown) can be modified in the scaling component 70 and compensation component 72 of FIG. 9 to accommodate this dependence.

The slope of the pressure response curve 151 is more affected by changes in the wall thickness of the conduit than is the density response curve 152. Therefore, by adjusting the flow conduit wall thickness for a particular design (in this example, an increase in wall thickness), the slope of the net resultant response curve 153 can be made to be nearly coincident with and parallel to the horizontal axis 157, thereby allowing the designer to work virtually anywhere along the horizontal axis 157 without errors resulting from either pressure or density for that particular fluid. As a practical matter, the net resultant response curve 153 is not, in general, linear and is therefore not coincident with the horizontal axis 157 over its entire length. However, the resulting error may be acceptable for many practical designs and will allow the designer to pick a convenient value for the exponential number n (either positive or negative, integer or noninteger) in the algorithm of equation (1) such as zero (using the velocity signals directly) or an integer real value to allow the use of a fundamental measurement method (displacement etc.).

A fourth embodiment of the present invention involves the determination of pressure, density or both and subsequent compensation for either or both of their effects on any arbitrary flow conduit geometry. The preferred method to determine the pressure, density or both for this embodiment is to vibrate the sensor in two natural modes of vibration simultaneously, with the restriction that the vibrational response of the device to changes in either pressure or density must be different for the two different modes. This difference allows for simultaneous solution of the pressure and density and subsequent compensation according to the device's characteristic curves. This embodiment has no restrictions on where the pressure or density sensitivity curves intersect zero or each other, thereby allowing maximum freedom to the designer to optimize any chosen design attribute such as conduit length, conduit walls thickness or magnet weight and to apply that geometry to any fluid to be measured.

Figure 13:
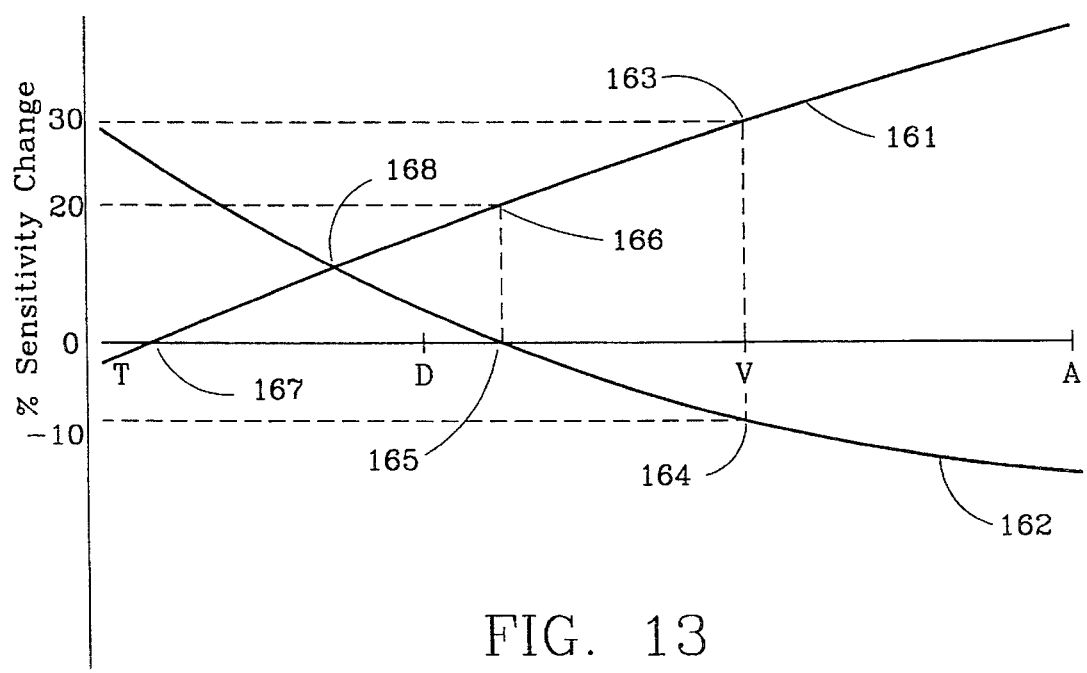
FIG. 13 illustrates a graph of curves representing a change in sensitivity of the Coriolis mass flow meter device of FIG. 1 due to changes in pressure and density, where the curves intersect each other at a non-zero value.

FIG. 13 depicts pressure and density sensitivity curves 161, 162 respectively for a representative flow conduit geometry. FIG. 13 depicts the pressure and density response curves 161 and 162 having zero intercepts 165,167 that are not coincident and an intersection 168 that is not a zero value. As previously mentioned, the zero intercepts 165, 167 are normally close to each other, however it is possible to get large separations between the two by design. Therefore FIG. 13 serves as a good example for the fourth embodiment where the slopes and intercepts of these response curves are not restricted.

Using the simultaneous solution method (described in detail hereinafter) the value of pressure and density are both determined and their effects compensated for. For example, referring to FIG. 13, if velocity signals are used for motion detection, then the necessary value for pressure compensation is the negative of the working point 163 of the curve 161, or approximately −30% per 1000 psi (since the response is positive with pressure, the compensation should be negative). Similarly the working point 164 on the curve 162 indicates a density compensation value of 8% per 1 gram/cc. Using the simultaneous solution method, the values of pressure and density are both accurately determined and then applied in conjunction with the aforementioned compensation values to correct the resultant signals for both pressure and density. For this example, if the pressure was determined to be 250 psi, then the pressure compensation value is:

250 psi*(−30%/1000 psi)=−7.5% compensation value.

Similarly, if the density was therefore determined to be 0.5 gm/cc then the density compensation value is:

0.5 g/cc*(8%/1 g/cc)=4% compensation value.

To use the simultaneous solution method, for determination of both pressure and density, two modes of vibration are excited on the sensor at the same time, with the requirement that their natural frequencies must change as a function of pressure or density at different rates.

Figure 14:
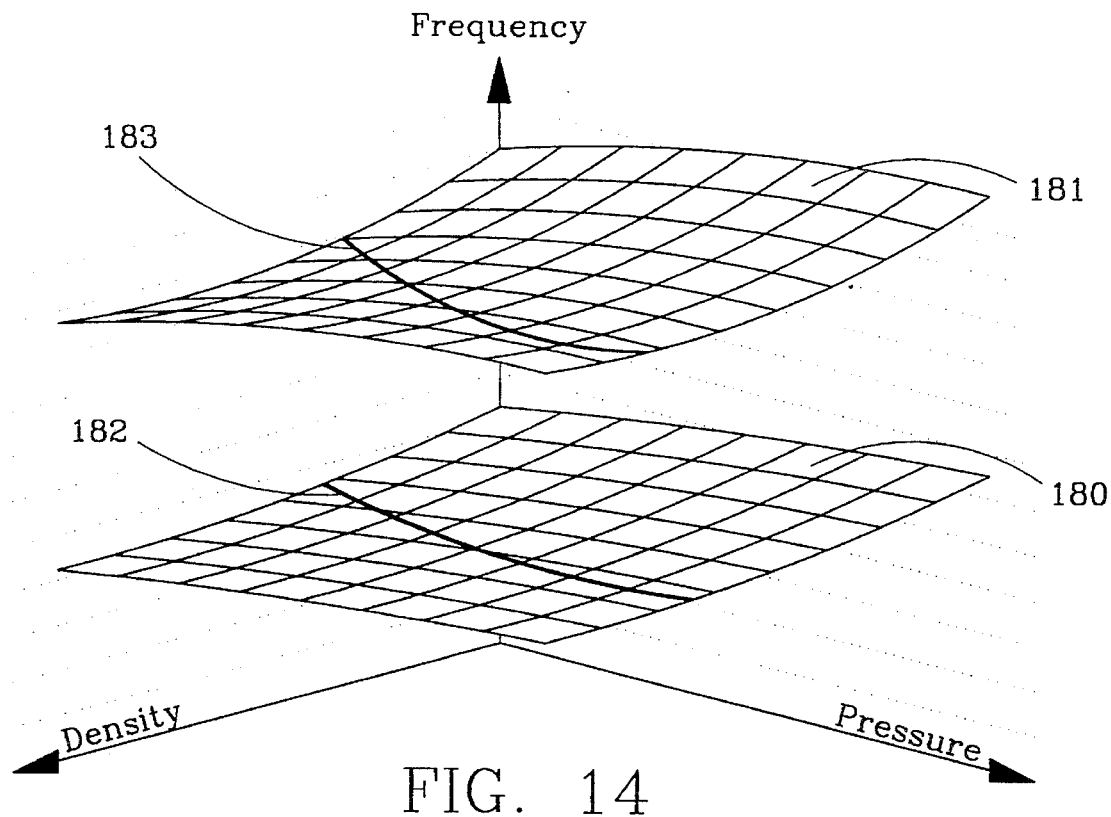
FIG. 14 illustrates an isometric view of two mathematical surfaces describing a range of natural frequencies for the first and third elliptical radial modes of vibration, resulting from various combinations of pressure and density.

FIG. 14 is an isometric view of a three axis graph depicting a pressure (right axis), density (left axis) and frequency (vertical axis), relationship for two radial modes of vibration for the sensor geometry of FIG. 1. A surface 180 depicts frequency values for various combinations of pressure and density for the first elliptical radial mode of vibration. Similarly, a surface 181 depicts frequency values for various combinations of pressure and density for the third elliptical radial mode of vibration. The surfaces 180, 181 are mathematical representations and are determined in a compensation factor determination process by subjecting a vibrating sensor to various combinations of pressure and density to determine a representative number of frequency values. Visual inspection of the surfaces 180, 181 indicate that, for both modes, frequency increases as pressure increases and decreases as density increases, but in different amounts. Other factors that affect these natural frequencies include temperature, conduit stress and viscosity. However, these other variables can be separately measured via temperature sensors, strain gages, drive power measurements or other similar means and are therefore not included as independent variables in the simultaneous solution.

During operation, both modes of vibration are excited and their frequency values determined. Knowing the frequency of each mode then allows a mathematical determination of a plane of constant frequency intersecting each of the surfaces 180, 181. The intersection of a plane of constant frequency and either of the surfaces 180,181 thereby defines a curve of constant frequency 182 thereon. The constant frequency curve 182 is therefore representative of all the possible combinations (within the limits of the graph) of pressure and density that causes that particular frequency for the first elliptical radial mode of vibration. Similarly, a constant frequency curve 183 is representative of all possible combinations of pressure and density that cause that particular frequency for the third elliptical radial mode of vibration.

Figure 15:
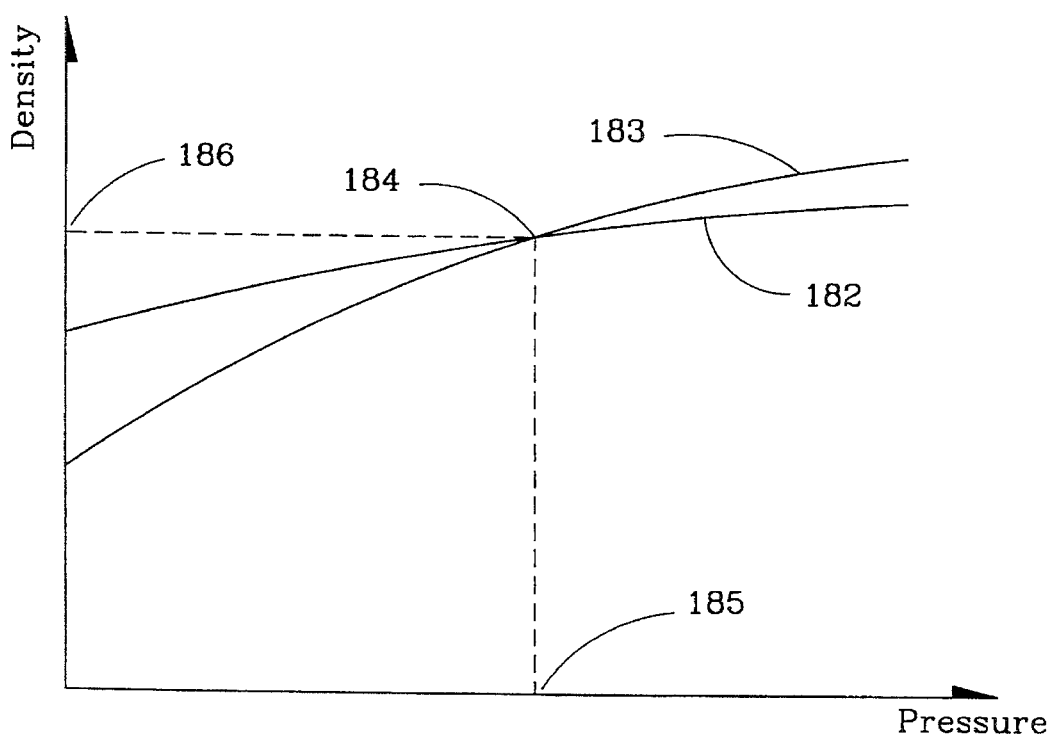
FIG. 15 illustrates a view down a frequency axis of FIGURE 14 showing a relationship and an intersection of the two constant frequency lines for the first and third elliptical radial modes of vibration as functions of pressure and density.

FIG. 15 is another view of the graph of FIG. 14, but viewed parallel to the frequency (vertical) axis and perpendicular to the pressure/density plane. Because of the different shapes of the surfaces 180, 181 of FIG. 14, the curves 182, 183 are not parallel to each other and, in this view, intersect each other at a solution point 184. The solution point 184, therefore represents the only combination of pressure 185 and density 186 that can cause the aforementioned two frequencies to occur at the same time. Therefore, by solving for this intersection working point, the pressure 185 and density 186 can be simultaneously determined and their values used for appropriate compensation as previously mentioned.

This embodiment is therefore rendered insensitive to pressure and density by virtue of its geometry in combination with direct solution of both pressure and density by the method of simultaneous solution and direct application of appropriate compensation factors. The embodiment therefore represents the highest degree of geometric design freedom to optimize any desired attribute, but requires the most sophisticated signal processing to effect the simultaneous solution.

Figure 16:
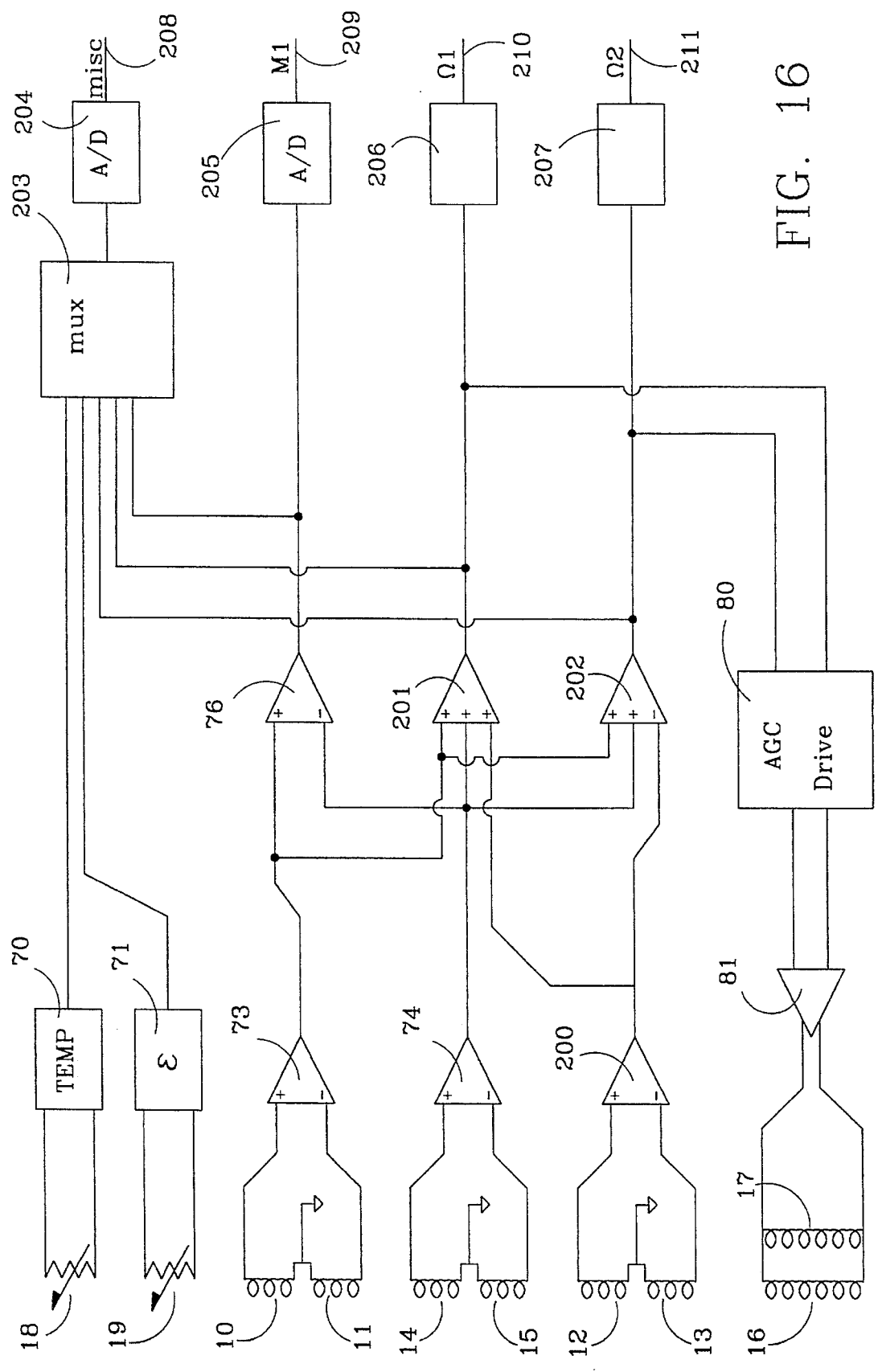
FIG. 16 illustrates an exemplary circuit diagram for processing the signals of the present invention.
Figure 17:
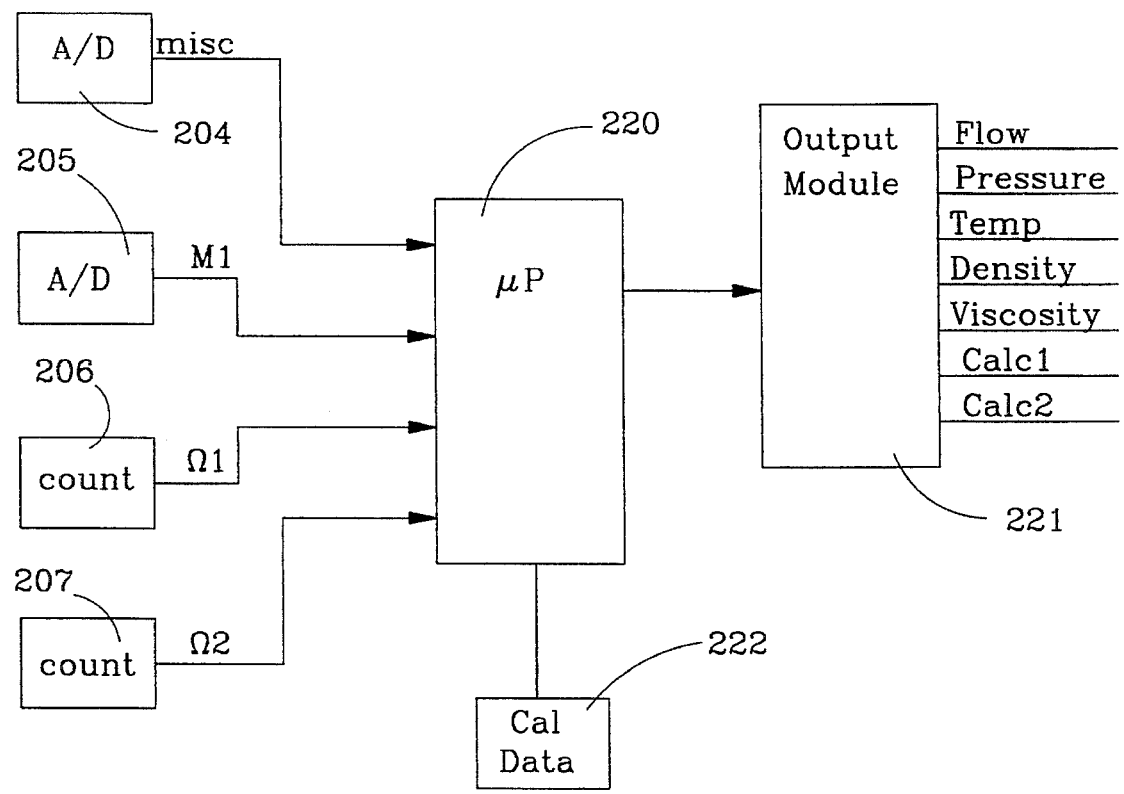
FIG. 17 illustrates a portion of an exemplary circuit diagram for processing the signals of the present invention.

FIGS. 16 and 17, taken together, depict a signal processing circuit that can be used in conjunction with the sensor geometry of FIG. 1 for this fourth embodiment. FIGS. 16 and 17 include many of the circuit components used previously in FIG. 9 and further include additional components related to sensing and driving the requisite secondary mode of vibration and effecting the simultaneous solution.

To use this fourth embodiment, the geometry of FIG. 1 is excited in two modes of vibration simultaneously, the first mode preferably being. the first elliptical radial mode (as shown in FIG. 3) and the second being the third elliptical radial mode (as shown in FIG. 5). These vibrations are sensed via the magnet/coil pairs 10 through 15. However, for this embodiment, the magnet/coil pairs 12, 13, being located midway down the length of flow conduit 1, sense the motion of the third elliptical radial mode (as shown in FIG. 5) in a phase opposite (180°) from that sensed by the other magnet/coil pairs 10, 11, 14, 15. This 180° phase inversion is used by summing and differential op-amps 201, 202 of FIG. 16 to sum appropriate amounts of the signals received from each magnet/coil pair to separate the first elliptical radial mode $\Omega 1$ from the third elliptical radial mode $\Omega 2$. The summing op-amp 201 sums signals from all 6 magnet/coil pairs, reinforcing the $\Omega 1$ signals, since they are all in the same phase. However, for the second mode $\Omega 2$, signals from the magnet/coil pairs 12, 13 are 180° out of phase compared to those of 10, 11, 14, 15. Therefore, by amplifying the signals appropriately from the differential op-amps 73, 74, 200, a cancellation of Ω2-related signals is accomplished in the summing op-amp 201, thereby isolating the Ω1-related signals. Similarly, using the same technique, the differential op-amp 202 thereby reinforces Ω2-related signals and cancels Ω1-related signals. By isolating these two signals from each other, each can be separately controlled for amplitude purposes and each can be accurately measured for use in obtaining a simultaneous solution. Ω1 and Ω2 signals from the components 201, 202, respectively, are both delivered to an AGC drive 80 and a power driver 81 to reinforce and control each mode's amplitude. In addition, Ω1 and Ω2 signals from the summing and differential op-amps 201, 202 are sent to analog to digital ("A/D") frequency converters 206, 207, respectively, that convert the signals from analog sine waves to digital numbers representing their frequencies. These numbers are then sent to a microprocessor 220 that uses these values to develop the simultaneous solution.

To use the simultaneous solution method, the pressure-versus-density-versus-frequency characteristics of a particular design must be determined to define mathematically the equations for the surfaces 180, 181. This is most accurately done through a compensation factor determination procedure by subjecting the sensor to various pressures and densities and noting the resulting frequencies for both Ω1 and Ω2. With a number of specific frequency working points known, both surfaces 180, 181 can be mathematically defined as a function of frequency as follows.

$$\Omega 1 = F1_o + (C1)*P - (C2)*D - (C5)T + (C6)\epsilon - (C9)v \quad (2)$$

$$\Omega 2 = F2_o + (C3)*P - (C4)*D - (C7)T + (C8)\epsilon - (C10)v \quad (3)$$

Where:

Ω1,Ω2 Measured Frequency for first and second modes of vibration, respectively (Hz);

$F1_o$, $F2_o$ Zero pressure/density frequency values for both modes, respectively (Hz);

C1–C10 Constants determined for each sensor or design. (Hz/psi, Hz/g/cc etc.);

P Fluid Pressure (psi);

D Fluid Density (g/cc); and

T,ϵ,v Temperature, Axial stress, Viscosity. These variables can be separately measured via the sensor 18 and strain gage 19 and need not be carried as independent variables in the simultaneous solution.

For the given sensor geometry for this fourth embodiment, the actual values for the pressure and density-related coefficients are similar to the following: (The temperature, stress and viscosity related terms can be separately measured and added as constants to the following equations, but for simplicity are not shown here.)

$$\Omega 1 = 2951 + (0.7)*P - (16.65)*D \quad (4)$$

$$\Omega 2 = 4408 + (0.51)*P - (25.9)*D \quad (5)$$

These two equations therefore define the three dimensional surfaces 180, 181 in terms of pressure, density and frequency for both modes of vibration. It is important to note that the coefficients preceding the pressure and density terms of equations (4) and (5) above have different values thereby according different slopes to the surfaces 180, 181. These differences are necessary to cause the curves 182,183 to intersect in the plane of FIG. 15 and thereby allow a simultaneous solution. The larger the slope differences between surfaces 180, 181, the more divergent the curves 182, 183 are and the more accurately their solution point 184 can be determined.

Next, the meter is placed in operation and the actual in-situ Ω1 and Ω2 frequencies are determined in the A/D frequency converters 206, 207 and their values delivered to the microprocessor 220. This reduces equations (4) and (5) above to functions of pressure and density only and in effect define the two curves 182, 183 of FIGS. 14 and 15.

Next, the one unique solution to these two equations (pressure 185 and density 186) are determined in the microprocessor 220 using the Newton-Raphson method of simultaneous solutions. This method uses the two equations (4) and (5) and their derivatives to solve for two equations with two unknowns where the equations can be non-linear. Since the equations (4) and (5) above are in polynomial form, their derivatives are easily determined. While equations (4) and (5) above are linear in nature, the actual surfaces 180, 181 will have a nonlinear component. For higher accuracies, these nonlinear components can also be added to equations (4) and (5) since the Newton-Raphson method can solve for nonlinear equations as well. In lieu of supplying the equations and derivatives in polynomial form, tables of values can be supplied in the form of a look up table. This method simplifies necessary curve fitting to reduce the data describing the surfaces 180, 181 into polynomial form and lends itself to accurately describing the nonlinear characteristics of the surfaces 180, 181.

For a reference to the described simultaneous solution method and a sample of computer code to implement it, refer to the book "Numerical Recipes in C", Cambridge University Press, second edition, ISBN 0-521-43108-5, §9.6 entitled, "Newton-Raphson Method for Nonlinear Systems of Equations." Using this method in conjunction with equations (4) and (5), the solution point 184 can be determined and its corresponding values for pressure 185 and density 186 are thereby determined.

The circuit of FIG. 16 further uses temperature signals from the scaling component 70 and strain-related signals from the scaling component 71, obtaining the signals via a multiplexer 203 and an A/D converter 204. In addition, the multiplexer 203 also receives signals from the differential and summing op-amps 76, 201, 202 to allow the microprocessor 220 to control various other aspects of the circuit, for example, the gain settings of the scaling and compensation components 70, 71, 73, 74,200, as well as controlling the amplitudes of both modes of vibration. Flow-related velocity signals from the differential op-amp 76 are converted to digital values 209 in the A/D converter 205 and sent to the microprocessor 220. Therefore, the microprocessor 220 receives the values of Ω1 210 and Ω2 211 from the A/D frequency converters 206 and 207, the value of flow-related velocity signals 209 from the A/D converter 205 and the values of temperature, strain, Ω1 and Ω2 driven velocities and others 208 from the A/D converter 204. In addition, the microprocessor 220 receives coefficient data defining the characteristics of the sensor (coefficients 1 through 10 of equations (2) and (3) above) from the storage component 222. These signals therefore comprise the necessary information to effect the simultaneous solution and render the necessary compensation.

Referring now to FIG. 13, with the pressure and density values now determined, the correct compensation values corresponding to the working points 163 (for pressure) and 164 (for density), can be directly applied in the microprocessor 220. In addition, the microprocessor 220 compensates for temperature, axial stress and viscosity, as necessary.

Finally, the microprocessor 220 supplies information to an output module 221 that can create output signals to the user including mass flow rate, pressure, density, temperature, viscosity and other calculated values. These output signals can further be used to control process equipment coupled to the mass flow meter, such as pumps to maintain a proper flow rate; valves to maintain a proper fluid density or viscosity; or temperature regulators to maintain a proper temperature.

Under certain circumstances, the simultaneous solution method may prove more accurate for solving for pressure than density or vice versa. An example of this is highly incompressible gasses, such as hydrogen, where the density is very low and changes little with large changes in pressure. Therefore, as a modification to this fourth embodiment, higher accuracies may be attained by a combination of applying the previously-defined algorithm of equation (1) of the second embodiment to eliminate the effects of one parameter, for example density, and then directly compensating for the other parameter, for example pressure, using the pressure value determined by the simultaneous solutions. This greatly reduces the accuracy requirement of the simultaneous solution since no compensation for density is needed and a much smaller compensation for pressure is used.

For this example, where the pressure and density response curves are as shown in FIG. 13, the flow-related velocity signal (M1) 209 of FIG. 16 is divided by a function proportional to $(\Omega 1)^{-7}$ to shift the working point from velocity to a working point 165, to eliminate the effect of density alone. Then, using the determined value of pressure from the simultaneous solution, a pressure-compensation value is directly determined from a working point 166 on the curve 161 and the appropriate compensation value directly applied, or approximately 20% per 1000 psi for this example.

This fourth embodiment therefore is inherently insensitive to pressure, density, temperature and axial stress by virtue of its geometry in combination with the algorithm of equation (1) and direct compensation using the determined values for pressure, density or both from the simultaneous solution and direct temperature and conduit strain measurements.

The four embodiments of the present invention just described eliminate the effects of pressure, density, temperature and axial stress by dealing with the response characteristics of a given sensor design with different signal processing methods. In the first embodiment, the geometry was designed to have the pressure, density and temperature response curves intersect each other and zero coincident with a fundamental measurement method (velocity). The second embodiment forces the pressure and density response curves to intersect zero at the same working point but not coincident with a fundamental measurement method, etc. For a designer to decide which embodiment is best for a particular application, the designer needs to know how to control the slope and zero intercept of the pressure and density response curves for a prospective design. The following discussion therefore gives guidelines with respect to controlling these response characteristics.

The slopes and zero intercepts of the response curves in FIGS. 7, 8, 12 and 13 are manipulated by adjusting the mass and stiffness properties of the vibrating portion of the conduit assembly. For the sensor geometry of FIG. 1, the manipulation of stiffness properties is accomplished by modifying the conduit diameter, wall thickness, elastic modulus and conduit length, while the manipulation of mass properties is accomplished by modifying the conduit density and the number, size and location of individual lumps of mass on the conduit.

While individual lumps of mass can be non-functioning, the necessary mass at a location can usually be combined with the functionality of a motion driver or motion detector by making the mass a magnet, a coil or some other type of motion driver or detector. It is important to realize that the effects of manipulating these design parameters are highly interrelated. For example, increasing the wall thickness of the conduit not only increases the stiffness to radial vibrations, it also increases the mass of the conduit uniformly and diminishes the effect of individual lumps of mass located on the conduit. Therefore, keeping in mind that changing one aspect of the sensor geometry effects many others and that the effect of a single change is not absolutely deterministic without analysis, general trends can be identified and will now be discussed giving the designer sufficient capability to control response curve shapes and intercepts.

Figure 18:
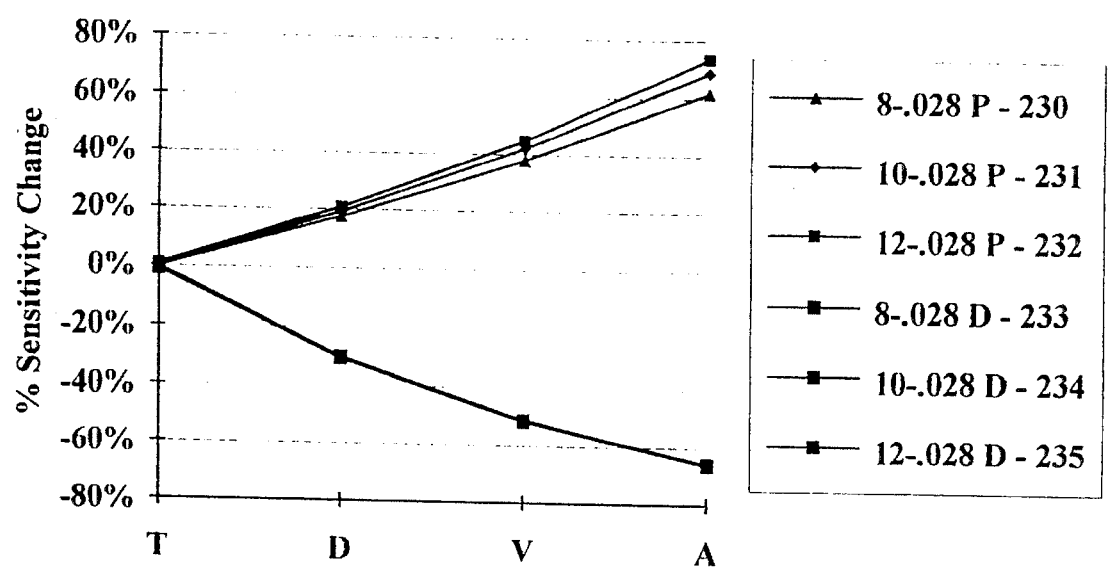
FIG. 18 depicts pressure and density response curves for several Coriolis mass flow meter conduit lengths without added masses.

In general, a single straight flow conduit without any extra masses placed upon it has pressure and density response characteristics similar to those depicted in FIG. 18. This figure compares the pressure and density response characteristics of three 1" diameter, 0.028" wall thickness stainless steel flow conduit geometries without any additional lumped masses. Data sets 230, 233 are the pressure and density response curves for an 8" long conduit, data sets 231 and 234 are for a 10" long conduit and data sets 232, 235 are for a 12" long conduit. One important aspect of the data sets 230, 231, 232, 233, 234, 235 of FIG. 18 is that their zero intercepts all closely converge on the time delay signal processing method on the left. This is a natural characteristic of a perfectly round straight conduit with uniform mass distribution (no additional masses) and uniform stiffness distribution (no added stiffness e.g. from brazed-on magnet hardware or changes in the wall thickness). If a bare conduit can be excited into the requisite mode of vibration and that motion sensed without adding any localized masses or stiffness (such as magnets) then the working point on the horizontal axis of FIG. 18 is the time delay method at the far left. As a practical matter however, to cause the requisite vibration and sense its motion, motion drivers and sensors are normally employed that add localized mass and stiffness properties to the conduit that alters these response curves away from converging on time delay.

Figure 19:
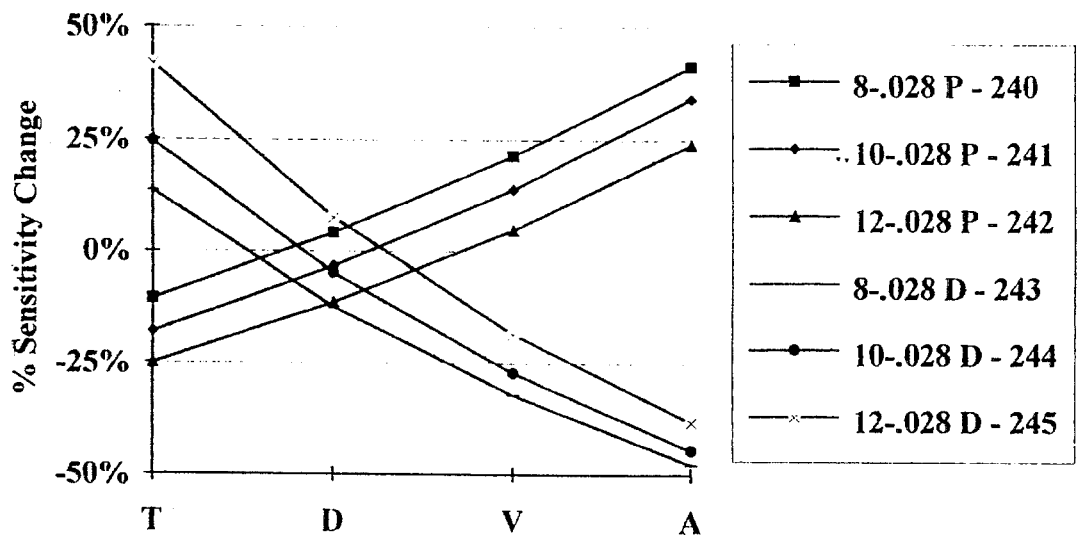
FIG. 19 depicts pressure and density response curves for the conduits of FIG. 18 with added center masses.

To exemplify the effect of adding two 0.185 ounce masses at the center of a conduit similar to the magnet/coil pairs 16, 17 on the flow conduit 1 of FIG. 1, the resulting response curves for the three conduit lengths of FIG. 18 are plotted in FIG. 19. Comparing the bare conduit response curves of FIG. 18 to those in FIG. 19 indicates that the addition of center mass reduces the slopes of the response curves and shifts their zero intercepts to the right of the time delay method by varying amounts depending on the conduit length.

Figure 20:
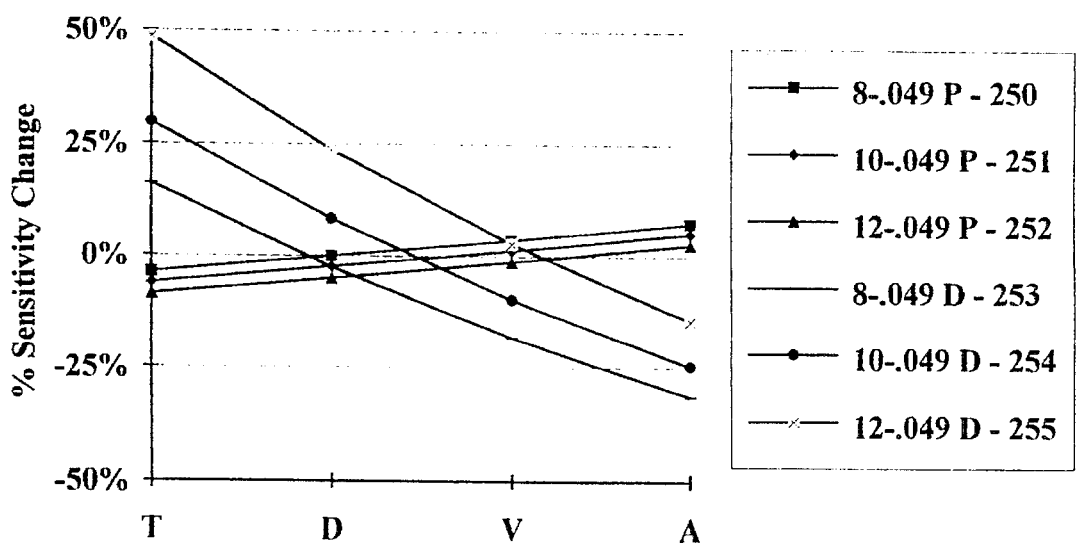
FIG. 20 depicts pressure and density response curves for the conduits of FIG. 19 with added outer masses.

FIG. 20 depicts the response characteristics of the same three conduit lengths and center masses of FIGS. 19 but with an increase in wall thickness to 0.049". The effect of this increase in wall thickness further reduces the slopes of the response curves and further shifts the zero intercepts of the response curves to the right.

The effect of adding outer masses, such as the magnet/coil pairs 10, 11, 14, 15 on the flow conduit 1 of FIG. 1, varies depending on how much the pairs 10, 11, 14, 15 weigh in comparison to center masses of the drive coils 16, 17 and their position along the length of flow conduit 1. If the outer masses are located close to the center masses, the outer masses exacerbate the effect of the center masses. Alternately, if the outer masses are located near the conduit ends (near the manifolds 4, 5 of FIG. 1) the effect of the outer masses is negligible. If the outer masses are located midway between the conduit ends and the center masses, the outer masses detract from the effect of center masses.

Therefore, the following Table II summarizes the general effects of increasing any one particular design parameter as it pertains to the slope of the response curve, its zero intercept, the flow conduit frequency and the sensitivity.

TABLE II

| Design Parameter (Increases) | Response Curve Slope | Response Curve Intercept | Flow Conduit Frequency | Sensor Sensitivity |
|---|---|---|---|---|
| Conduit Length | Negligible | Shifts Right | Decreases | Increases |
| Wall Thickness | Decreases | Varies Negligibly | Increases | Increases |
| Elastic Modulus | Decreases | Varies Negligibly | Increases | Increases |
| Center Mass | Decreases | Shifts Right | Decreases | Decreases |
| Outer Mass | Varies | Varies | Decreases | Decreases |

As previously mentioned, the effects of changing any one design parameter are interrelated with the effects of the other parameters and, therefore, the final result of a single change is not absolutely deterministic without analysis.

The methods and algorithms delineated in the specification herein have been applied to Coriolis flow sensors with a single conduit vibrating in a radial mode of vibration, since that is a preferred embodiment. However, the control of the slope and intercepts of the various response curves and the algorithm of equation (1) also pertain to traditional bending mode type Coriolis flow meters as well. It is outside the scope of the Detailed Description to expound upon the effects of changing design parameters as they pertain to traditional bending mode Coriolis type flow sensors since there are currently many complex conduit shapes and geometries available ranging from simple straight conduits vibrating in the first bending mode to $\Omega$-shaped conduits vibrating in second order bending or twist modes.

Given all the possible design parameters for bending mode conduit geometries, it is impractical to construct a simplified summary of their effects on response as in Table II, above. However, the basic principles are the same in that by appropriate application of localized mass and stiffness properties upon the flow conduit, the response curves of a given bending mode sensor can be controlled so that the zero intercepts coincide with each other at some working point along the horizontal axis, wherein the appropriate value of n for the exponent of equation (1) can be applied to correct for pressure and density at the same time. Alternately, if the response curves do not intersect at a zero value, the method of simultaneous equations as explained above for radial mode meters can be applied to bending mode meters to calculate directly the pressure and density and directly compensate for those errors.

Figure 21:
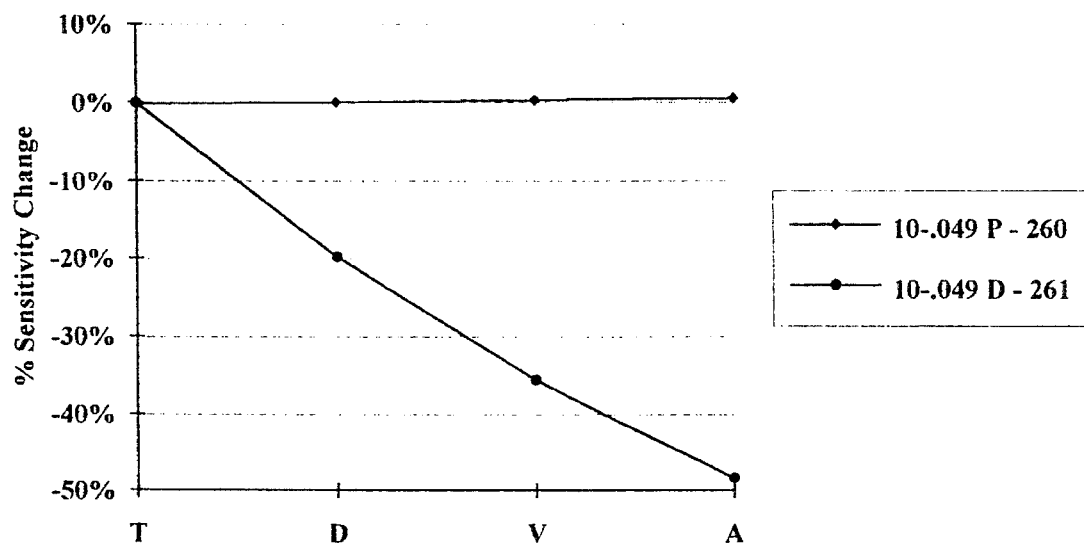
FIG. 21 depicts pressure and density response curves for a conduit operating in a first bending mode of vibration without added masses.

As an example, FIG. 21 depicts pressure and density response curves 260, 261 for a 10" long, 0.049" wall thickness stainless steel conduit with no masses on the conduit and operating in the first bending mode of vibration. Since there are no added localized masses or stiffnesses on this example, it is comparable to the graph of FIG. 18 (a radial mode meter with no added masses).

Comparing FIGS. 21 to 18 indicates that, in general, a bare flow conduit without added masses or stiffnesses has response curves that tend to converge near the time delay method on the left side of the graphs. Another observation that can be made between FIGS. 18 and 21 is that the slope of the pressure response curve 260 in the bending mode is significantly less than the slope of the curves 230 through 232 operating in the radial mode. This slope difference is due to the fact that bending mode vibrations are not as greatly affected by internal pressure as are radial modes of vibration. However, bending mode conduit designs having thinner walls and more convoluted shapes than this example, have increasingly higher slopes on their pressure response curves. Therefore, the error caused by pressure and density changes can be significant on bending mode meters and can be corrected using the methods described herein for radial mode meters.

Figure 22:
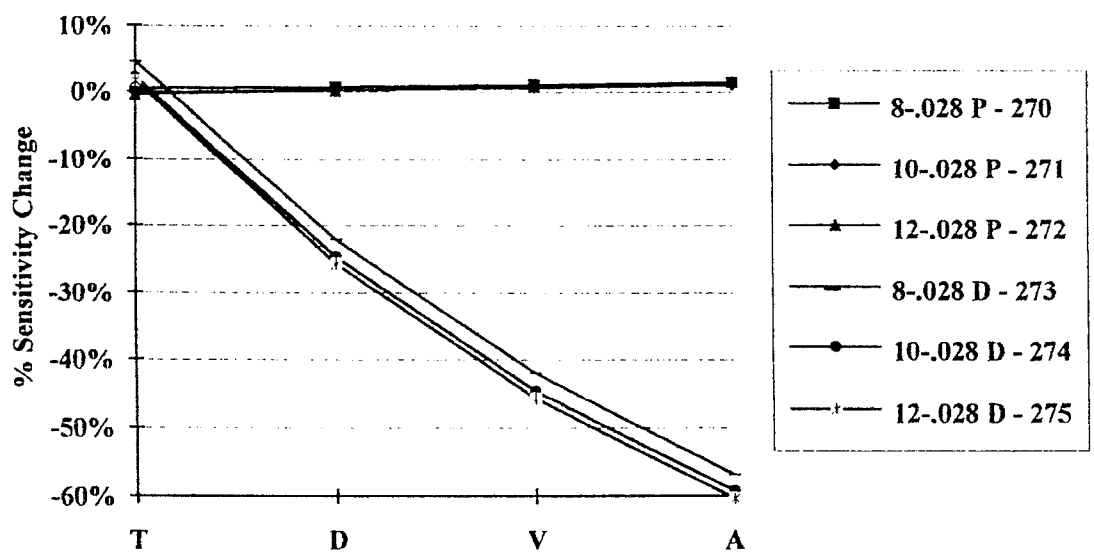
FIG. 22 depicts pressure and density response curves for a conduit operating in the first bending mode of vibration with added masses.

As with radial mode meters, localized masses and stiffnesses are normally added to a bare flow conduit operating in a bending mode of vibration as necessary for motion drivers and sensors. The effects of these added masses and stiffnesses are similar to those on radial mode meters. FIG. 22 therefore is a final example of the applicability of the present invention as it applies to bending mode meters. Pressure response curves 270 through 272 and density response curves 273 through 275 indicate the response of conduit lengths of 8", 10" and 12", with 0.028" wall thickness, of stainless steel, operating in the first bending mode of vibration and with two 0.185 ounce drive masses at the center of the conduit length. These response curves show the susceptibility of bending mode meters to localized masses and stiffness and show that the algorithm of equation (1) can be advantageously applied on bending mode meter designs as well. For the example of FIG. 22, using the 8" long conduit having the corresponding response curves 270, 273 and assuming velocity sensors were used to acquire the flow signals, an exponent value of approximately 1.8 in equation (1) can be used to correct for most of the pressure and density-related errors on these signals.

From the above, it is apparent that the present invention provides a Coriolis mass flow meter comprising: (1) a flow conduit for containing a fluid having a physical characteristic, the fluid adapted to flow in the conduit at an unknown rate, (2) a drive circuit for creating a vibration in the flow conduit, the fluid altering the vibration as a function of the physical characteristic and the flow rate, (3) a detector circuit for measuring the altered vibration at a working point and producing a signal representing an uncompensated mass flow rate of the fluid and (4) a computation circuit for calculating a compensated mass flow rate of the fluid proportional to the uncompensated rate by $1/\Omega 1^n$, where $\Omega 1$ is a driven natural frequency of the flow conduit and n is a number chosen as a function of the working point, the compensated rate thereby reduced of effects of the physical characteristic.

Although the present invention and its advantages have been described in detail, those skilled in the art should understand that they can make various changes, substitutions and alterations herein without departing from the spirit and scope of the invention as defined by the appended claims.

What is claimed is:

1. A method of determining pressure and density with a Coriolis mass flow meter, comprising the steps of:

providing a flow conduit for containing a fluid having a pressure and a density, said flow conduit having a predetermined length, radius and wall thickness;

causing said fluid to flow in said conduit at a given rate;

simultaneously creating two natural modes of vibration in said flow conduit with a drive circuit, said fluid altering said modes of vibration as a function of said pressure, density, flow rate, material, length, radius and wall thickness;

measuring one of said altered modes of vibration with a detector circuit at a working point, said detector circuit producing a first signal representing an uncompensated mass flow rate of said fluid; changing said pressure and density of said fluid;

measuring another of said altered modes of vibration with said detector circuit at said working point, said detector circuit producing a second signal representing an uncompensated mass flow rate of said fluid;

computing said pressure and density by simultaneous solution, said simultaneous solution further providing a compensation factor relating to said material, length, radius and wall thickness of said flow conduit; and providing a computation circuit for said meter embodying said compensation factor.

2. The method as recited in claim 1 wherein said step of computing comprises the step of simultaneously solving:

$$\Omega 1 = F1_o + (C1)*P - (C2)*D - (C5)T \text{ and}$$

$$\Omega 2 = F2_o + (C3)*P - (C4)*D - (C7)T$$

where:

$\Omega 1$ and $f\Omega 2$ = measured frequencies of said first and second signals;

$F1_0$ and $F2_o$ = zero pressure/density frequency values for said modes of vibration, respectively;

C1–C10 = predetermined constants;

P = said pressure; and

D = said density.

3. The method as recited in claim 1 further comprising the step of measuring a temperature and axial stress of said flow conduit and a viscosity of said fluid.

* * * * *

UNITED STATES PATENT AND TRADEMARK OFFICE
CERTIFICATE OF CORRECTION

PATENT NO. : 5,473,949
DATED : December 12, 1995
INVENTOR(S) : Donald R. Cage, et al.

It is certified that error appears in the above-indentified patent and that said Letters Patent is hereby corrected as shown below:

Col. 2, line 54, insert --so-- after "more".

Col. 15, line 1, insert --at-- after "meters,".

Signed and Sealed this

Twenty-first Day of May, 1996

*Attest:*

BRUCE LEHMAN

*Attesting Officer*     *Commissioner of Patents and Trademarks*